US007939116B2

(12) United States Patent
Nonaka et al.

(10) Patent No.: US 7,939,116 B2
(45) Date of Patent: May 10, 2011

(54) SULFUR-CONTAINING PROANTHOCYANIDIN OLIGOMER COMPOSITION AND PRODUCTION METHOD THEREOF

(75) Inventors: Gen-ichiro Nonaka, Saga (JP); Buxiang Sun, Hokkaido (JP); Lan Yuan, Hokkaido (JP); Takashi Nakagawa, Hokkaido (JP); Hajime Fujii, Hokkaido (JP); Young-Joon Surh, Seoul (KR)

(73) Assignees: Amino Up Chemical Co., Ltd., Hokkaido (JP); Usaien Pharmaceutical Co., Ltd., Saga (JP)

( * ) Notice: Subject to any disclaimer, the term of this patent is extended or adjusted under 35 U.S.C. 154(b) by 0 days.

(21) Appl. No.: 12/898,926

(22) Filed: Oct. 6, 2010

(65) Prior Publication Data

US 2011/0021792 A1    Jan. 27, 2011

Related U.S. Application Data

(62) Division of application No. 10/513,950, filed as application No. PCT/JP2004/007448 on May 25, 2004, now Pat. No. 7,833,553.

(30) Foreign Application Priority Data

May 26, 2003  (JP) .................... 2003-148276
Jan. 26, 2004  (JP) .................... 2004-017113

(51) Int. Cl.
*A61K 36/87*    (2006.01)
(52) U.S. Cl. ....................................... 424/766
(58) Field of Classification Search ............... None
See application file for complete search history.

(56) References Cited

U.S. PATENT DOCUMENTS 6,528,664 B2    3/2003  Romanczyk et al.
2008/0311580 A1*  12/2008  Abrahams et al. ............. 435/6

FOREIGN PATENT DOCUMENTS

WO    WO 03/024951 A1    3/2003

OTHER PUBLICATIONS

Hu et al., "Antioxidant of a proanthocyanidin-Rich Extract from Grape Seed in Whey Protein Isolate Stabilized Algae Oil-In-Water Emulsions", Journal of Agriculture Food Chemistry, 2004, pp. 5272-5276.*
Hong, Chuang-Ye, "The Inhibitory Effect of Tannins on Lipid Peroxidation of Rat Heart Mitochondria," Journal of Pharmacy and Pharmacology, vol. 47 ( No. 2), p. 138-142, (Nov. 3, 1995).
Kolodziej, Herbert, "Thiolysis of birch bark procyanidins: structural dependence in formation of 2, 3-cis-3, 4-cis-flavan-4-benzylthioethers from procyanidins," Phytochemistry, vol. 29 ( No. 5), p. 1671-1674, (Nov. 3, 1990).
Heimgway, Richard W. et al., "Heterogeneity of interflavanoid bond location in loblolly pine bark procyanidins," Phytochemistry, vol. 22 (No. 1), p. 275-281, (Nov. 3, 1983).
Foo, Lai Yeap et al., "Procyanidin dimers and trimers from Douglas fir inner bark," Phytochemistry, vol. 28 (No. 6), p. 1743-1747, (Nov. 3, 1989).
Geiss, Friederike et al., "Proanthocyanidins with (+)-epicatechin units from *Byrsonima crassifolia* bark," Phytochemistry, vol. 39 ( No. 3), p. 635-643, (Nov. 3, 1995).
Tanaka, Takashi et al., "Chemical evidence for the de-astringency (insolubilization of tannins) of persimmon fruit," Journal of the Chemical Society, Perkin Transactions 1: Organic and Bio-Organic Chemistry, p. 3013-3022, (Nov. 3, 1994).
Scholz, Eberhard et al., "Proanthocyanidins from *Krameria triandra* root," Planta Medica, vol. 55 (No. 4), p. 379-384, (Nov. 3, 1989).
Torres, J.L. et al., "Cysteinyl-flavan-3-ol Conjugates from Grape Procyanidins. Antioxidant and Antiproliferative Properties," Bioorganic & Medicinal Chemistry, p. 2497-2509, (Nov. 3, 2002).
English translation of Torres (WO 03/024951-3-2003).

* cited by examiner

*Primary Examiner* — Christopher Tate
*Assistant Examiner* — Deborah A. Davis
(74) *Attorney, Agent, or Firm* — Dennis G. LaPointe

(57) ABSTRACT

Provided are: method of producing a sulfur-containing proanthocyanidin oligomer by reducing the molecular weight of proanthocyanidin in plants so that they can be readily absorbed through the intestine of an organism; and a health food composition and a pharmaceutical composition which contain the resultant sulfur-containing proanthocyanidin oligomer as an active ingredient and which are useful for treating and preventing various lifestyle-related diseases and brain diseases caused by generation of active oxygen species as well as for preventing aging.

1 Claim, 13 Drawing Sheets a, b, c: Significant differences are indicated at 5% level between different symbols (Duncan's multiple test)

a: No significant difference is indicated at 5% level (Duncan's multiple test)

a, b, c: Significant differences are indicated at 5% level between different symbols (Duncan's multiple test)

a, b: Significant differences are indicated at 1% level between different symbols (Duncan's multiple test)

a, b: Significant differences are indicated at 1% level between different symbols (Duncan's multiple test)

(A)

INVENTIVE SUBSTANCE 1   COMPARATIVE SUBSTANCE 1

(B)

| β-AMYLOID | − | + | + | + |
| INVENTIVE SUBSTANCE 1 | − | − | + | − |
| COMPARATIVE SUBSTANCE 1 | − | − | − | + |

EFFECT OF SULFUR-CONTAINING PROANTHOCYANIDIN OLIGOMER ON BLOOD GLUCOSE LEVEL IN STZ-INDUCED DIABETES MODEL

EFFECT OF SULFUR-CONTAINING PROANTHOCYANIDIN OLIGOMER ON URINE GLUCOSE LEVEL IN STZ-INDUCED DIABETES MODEL

EFFECT OF SULFUR-CONTAINING PROANTHOCYANIDIN OLIGOMER ON URINE PROTEIN IN STZ-INDUCED DIABETES MODEL

EFFECT OF SULFUR-CONTAINING PROANTHOCYANIDIN OLIGOMER ON BLOOD LPO IN STZ-INDUCED DIABETES MODEL

EFFECT OF SULFUR-CONTAINING PROANTHOCYANIDIN OLIGOMER ON
BLOOD TEAC IN STZ-INDUCED DIABETES MODEL

EFFECT OF SULFUR-CONTAINING PROANTHOCYANIDIN OLIGOMER ON
BLOOD POLYPHENOL LEVEL IN POTASSIUM BROMATE-INDUCED
ACUTE RENAL INJURY MODEL

EFFECT OF SULFUR-CONTAINING PROANTHOCYANIDIN OLIGOMER ON
BLOOD ANTIOXIDANT CAPACITY (TEAC) IN POTASSIUM
BROMATE-INDUCED ACUTE RENAL INJURY MODEL

EFFECT OF SULFUR-CONTAINING PROANTHOCYANIDIN OLIGOMER ON
BLOOD LIPID PEROXIDE LEVEL IN POTASSIUM BROMATE-INDUCED
ACUTE RENAL INJURY MODEL

EFFECT OF SULFUR-CONTAINING PROANTHOCYANIDIN OLIGOMER ON BLOOD UREA NITROGEN LEVEL IN POTASSIUM BROMATE-INDUCED ACUTE RENAL INJURY MODEL

EFFECT OF SULFUR-CONTAINING PROANTHOCYANIDIN OLIGOMER ON BLOOD CREATININ LEVEL IN POTASSIUM BROMATE-INDUCED ACUTE RENAL INJURY MODEL

SULFUR-CONTAINING PROANTHOCYANIDIN OLIGOMER COMPOSITION AND PRODUCTION METHOD THEREOF

RELATED APPLICATION

This application is a divisional application of U.S. patent application Ser. No. 10/513,950 filed Nov. 9, 2004, which is a 35 USC 371 national stage application of PCT?JP2004/007448 filed May 25, 2004, which in turn claims priority from JP2003-148276 filed May 26, 2003 and JP2004-17113 filed Jan. 26, 2004.

TECHNICAL FIELD

The present invention relates to a sulfur-containing proanthocyanidin oligomer, a composition thereof, production method thereof, and use thereof. More specifically, the present invention provides method of producing a sulfur-containing proanthocyanidin oligomer by reducing the molecular weights of proanthocyanidins in plants to a level such that absorption through intestine of an organism is facilitated, a health food composition and a drug composition which contain the sulfur-containing proanthocyanidin oligomer obtained by the method as an active ingredient and which are useful for treatment and prevention of various lifestyle-related diseases and brain diseases caused by generation of active oxygen species or the like.

BACKGROUND ART

As a result of an excessive intake of fats due to changes of diet, changes in environment, increase in the exposure to ultraviolet rays due to destruction of the ozone layer, increases in environment pollutants and the like, the number of patients with so-called lifestyle-related diseases such as hyperlipemia, hypercholesterolemia, hypertension, diabetes and cancers is increasing and also the number of patients with allergy or brain diseases such as dementia is increasing. With a progress in aging of society, an increase in the number of patients with dementia, Alzheimer's syndrome, and the like in future is feared; it has been pointed out that active oxygen species generated in the organism are involved in these diseases (Bioorganic & Medicinal Chemistry, 10 (2002), 2497-2509). However, since no technology that completely suppresses or controls generation of active oxygen species has been developed yet, there are no established technologies which are sufficiently effective and reliable for preventing or treating lifestyle-related diseases, brain diseases, and the like at present.

In recent years, attention has been focused on natural substances that are found in plants and exhibit physiological activities, particularly polyphenol compounds. Polyphenols are generally contained in tea, vegetables, fruits, herbs, and the like and are expected to be useful as treating or preventive agents having no side effect, which has been confirmed from a long-term intake as a food or favorite.

Polyphenol compounds are secondary metabolites of plants and known to universally and abundantly occur in the plant world and exhibit various physiological activities. Polyphenol compounds have received attention in the field of pharmacology, plant chemistry, and the like since long ago, and are recently attracting attention from the filed of health food. For example, it is known that polyphenols in tea, particularly catechins, exhibit a wide variety of physiological activities such as antimicrobial effect, antiviral effect, anti-mutational effect, antioxidative effect, effect for preventing pressure increase, effect for lowering blood cholesterol, anticarious effect, antiallergic effect, effect for improving intestinal flora and deodorant effect.

Among polyphenols, proanthocyanidins are polyphenols that are contained in a wide variety of plants. In order for proanthocyanidins to exhibit various physiological activities as mentioned above, proanthocyanidin compounds have to be absorbed in an organism through intestine. However, proanthocyanidins are said to have molecular weights generally on the order of several thousands to several ten thousands. Substance having such a high molecular weight is difficult to be absorbed through the intestine. Even when the proanthocyanidins are taken in, in most cases, they are not absorbed into the living body, so that they are not utilized by the living organism.

The inventors of the present invention have found that a polyphenol extracted from buckwheat has activities of improving lipid metabolism, brain function, and so on and filed a patent application (JP 10-218786 A) based on the findings. The active ingredient of the polyphenol is a proanthocyanidin polymer, and its bioabsorbability has been considered as less than sufficient.

DISCLOSURE OF THE INVENTION

The present invention is to provide a medicament, health food and the like that are useful for treating or preventing lifestyle-related diseases and brain diseases presumably caused by active oxygen species by converting a proanthocyanidin compound having a poor bioabsorbability through the intestine into a compound form readily absorbed into the living body and allowing various physiological effects of the proanthocyanidin compound to be fully exhibited so that the antioxidation activity of the living organism can be increased.

The inventors of the present invention have found that a sulfur-containing proanthocyanidin oligomer having a low molecular weight, which is obtained by a reaction between a plant containing proanthocyanidins or extract thereof and an SH group-containing compound can be readily absorbed into a living body through the intestine and exhibit various physiological activities by oral intake, and based on this finding, completed the present invention.

That is, the present invention relates to the following sulfur-containing proanthocyanidin oligomers and compositions thereof useful as pharmaceutical compositions and health food compositions as well as production methods for these.

1. A composition comprising a sulfur-containing proanthocyanidin oligomer as a main component, wherein the oligomer is obtained by concentrating and drying a reaction solution prepared by reacting a plant containing proanthocyanidins or extract thereof with an SH group-containing compound.
2. The sulfur-containing proanthocyanidin oligomer composition according to 1, wherein the oligomer is one selected from a dimer to pentamer of the proanthocyanidin.
3. The sulfur-containing proanthocyanidin oligomer composition according to 1, wherein the plant containing proanthocyanidins is one or more selected from a group consisting of vegetables, fruits, teas, herbs, spices, woods and barks.
4. The sulfur-containing proanthocyanidin oligomer composition according to 1, wherein the SH group-containing compound is at least one selected from a group consisting of cysteine, cystine, glutathione, SH group-containing peptides, and salts thereof.

5. The composition according to any one of 1 to 4, which is a pharmaceutical composition for treating and/or preventing lifestyle-related diseases.
6. The composition according to any one of 1 to 4, which is a pharmaceutical composition for preventing aging.
7. The composition according to any one of 1 to 4, which is a health food composition for alleviating and/or preventing lifestyle-related diseases.
8. The composition according to any one of 1 to 4, which is a health food composition for preventing aging.
9. A sulfur-containing proanthocyanidin oligomer, which is obtained by fractionating components containing a sulfur-containing proanthocyanidin oligomer prepared by reacting a plant containing proanthocyanidins or extract thereof with an SH group-containing compound.
10. The sulfur-containing proanthocyanidin oligomer according to 9, wherein the oligomer is one selected from a dimer to pentamer of proanthocyanidin.
11. A method of producing a sulfur-containing proanthocyanidin oligomer composition, wherein a plant containing proanthocyanidins or extract thereof is reacted with an SH group-containing compound under an acidic condition and the reaction solution is concentrated and dried.
12. A method of producing a sulfur-containing proanthocyanidin oligomer composition, wherein a plant containing proanthocyanidins or extract thereof is reacted with an SH group-containing compound under an acidic condition and the reaction solution is concentrated and fractionated.
13. The production method according to 11 or 12, wherein the plant containing proanthocyanidins is one or more selected from a group consisting of vegetables, fruits, teas, herbs, spices, woods, and barks.
14. The production method according to 11 or 12, wherein the SH group-containing compound is at least one selected from a group consisting of cysteine, cystine, glutathione, SH group-containing peptides and salts thereof.
15. The production method according to 11 or 12, wherein the acidic condition is obtained by using one or both of an inorganic acid and an organic acid.
16. The production method according to 15, wherein at least one selected from a group consisting of hydrochloric acid, sulfuric acid, nitric acid, acetic acid, citric acid, ascorbic acid, and malic acid is used.
17. A proanthocyanidin compound represented by Formula (4).

(4)

18. A proanthocyanidin compound represented by Formula (5).

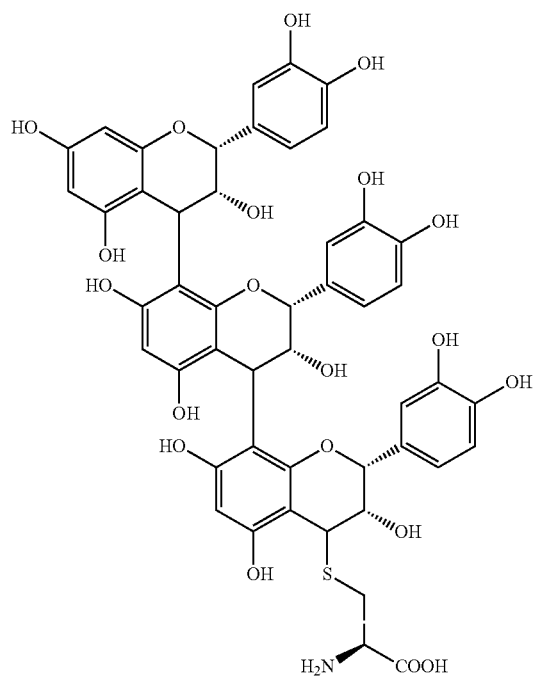

(5)

19. A proanthocyanidin compound represented by Formula (6).

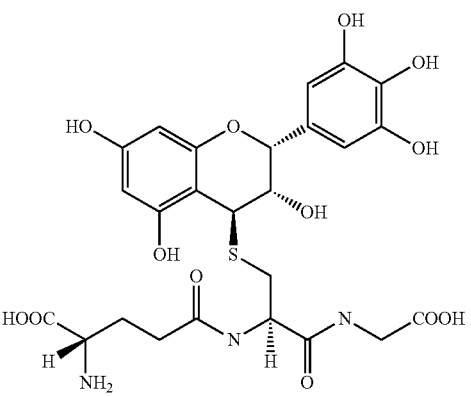

(6)

20. A proanthocyanidin compound represented by Formula (7).

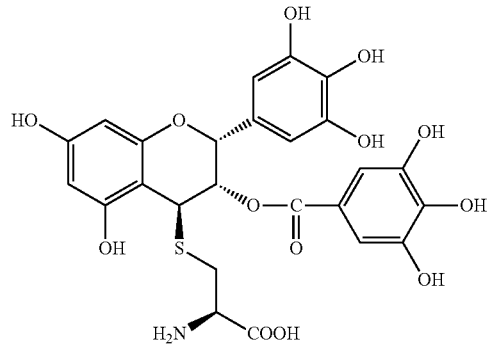

(7)

21. A proanthocyanidin compound represented by Formula (8).

(8)

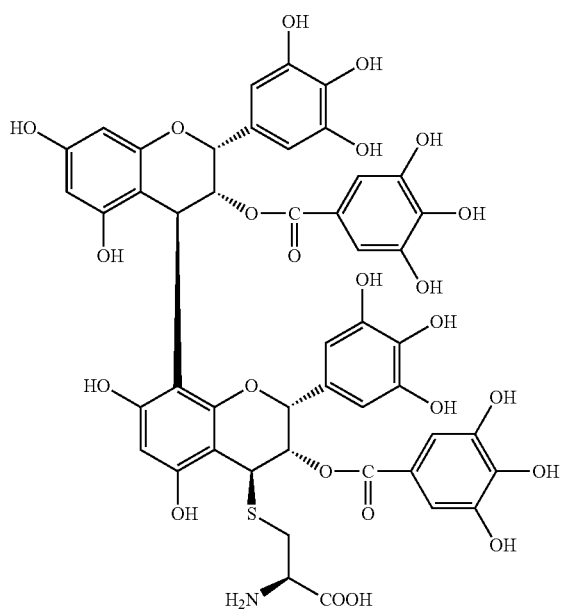

BRIEF DESCRIPTION OF THE DRAWINGS

FIG. 1A indicates results on low dose-administered groups and FIG. 13 indicates results on high dose-administered groups.

DETAILED DESCRIPTION OF THE INVENTION

Figure 1:
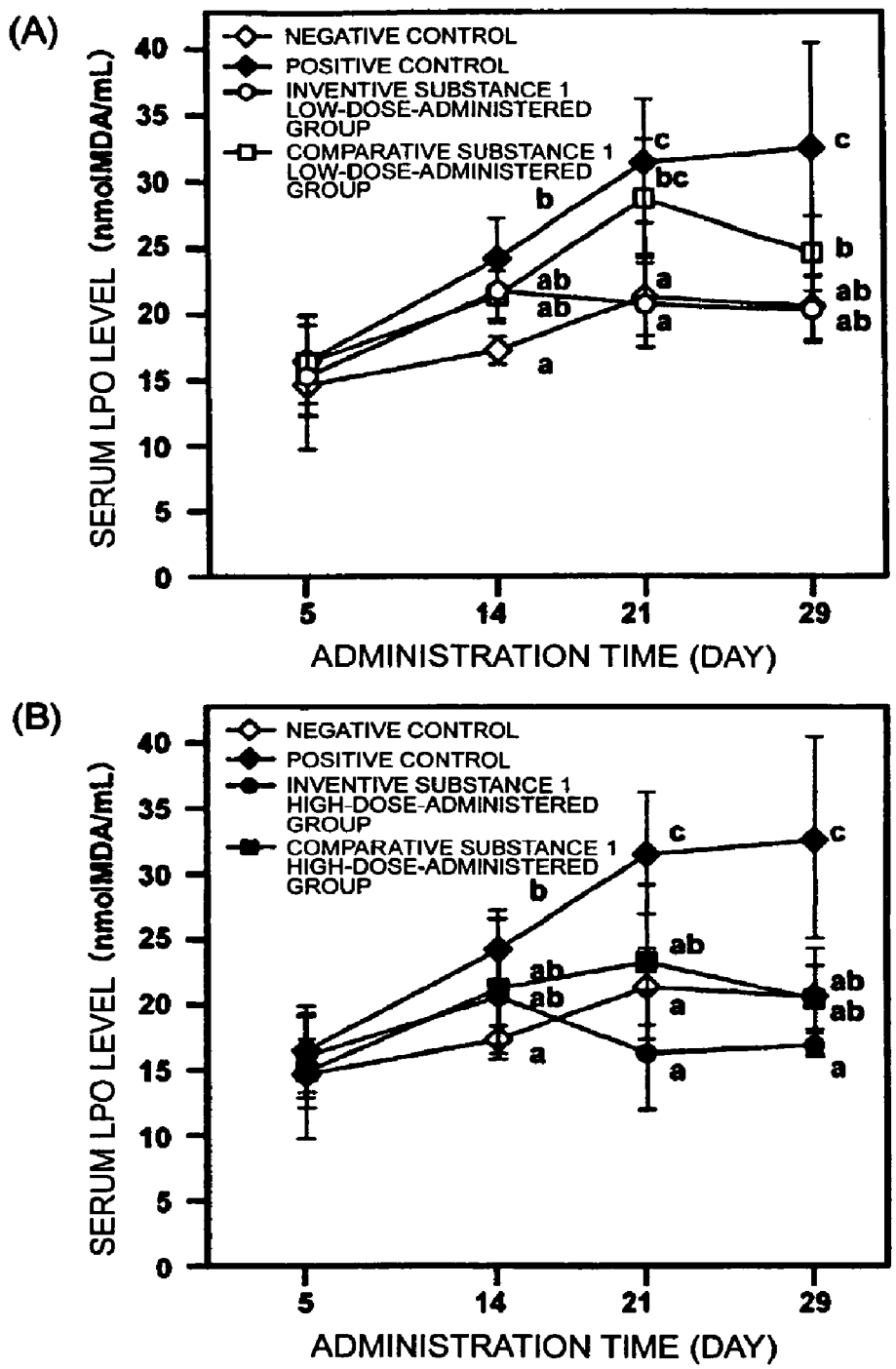
FIGS. 1A and 1B are graphs illustrating serum LPO levels in mice administered with a sulfur-containing proanthocyanidin oligomer composition according to Example 1 of the present invention (powder before fractionation; Substance 1) and its raw material (grape seed polyphenol extract; Comparative Substance 1).

The sulfur-containing oligomer of the present invention usually comprises dimer to pentamer of proanthocyanidin and usually has a molecular weight of 1,500 or less.

It is preferable that reaction between the plant containing proanthocyanidins or its extract with the SH group-containing compound be carried out under an acidic condition. Suitable acids selected from inorganic acids such as hydrochloric acid, sulfuric acid and nitric acid, and organic acids such as acetic acid, citric acid, ascorbic acid, and malic acid are used in concentrations of about 0.1 N to 1.0 N, preferably 0.5 N.

The term "proanthocyanidin" as used herein refers to catechin polymers, specific examples of which include catechin, epicatechin, epigallocatechin, epigallocatechin gallate, gallocatechin, and gallocatechin gallate as well as those which include these as constitutional units.

Plants that contain proanthocyanidins include a wide variety of plants including: vegetables and fruits such as Japanese persimmon, pear, grape, strawberry, banana, avocado, mountain cranberry, lotus root, and buckwheat; teas in general, such as green tea, black tea, and oolong tea; herbs and spices; and woods and pine barks. Those proanthocyanidin-containing plants and extracts (inclusive of pressed juice, fruit juice, and vegetable juice) thereof are preferably used.

Examples of the SH group-containing compound used in the present invention include cysteine, cystine, glutathione, SH-containing peptides, and salts thereof as well as sulfur-containing natural substances such as onion and garlic. Also, mercaptans are usable. However, in consideration that the sulfur-containing proanthocyanidin oligomer of the present invention is used in food and pharmaceutical compositions, the SH group-containing compounds used therein are preferably those which are acceptably used in food and pharmaceuticals.

The reaction between the plant containing proanthocyanidins or its extract with the SH group-containing compound is carried out at room temperature to 80° C., preferably 40 to 60° C. for a few hours to 1 week, preferably 24 to 48 hours.

Examples of solvent used in the reaction include water, methanol, ethanol and a mixture of two or more of them. However, in consideration for application to foods and pharmaceuticals, water and ethanol are preferable.

After the reaction, the residue is filtered and the filtrate is concentrated. After that, the concentrate is purified in a conventional manner.

That is, purification of the concentrate can be carried out by subjecting the obtained extract to membrane treatment (ultrafiltration, reverse osmosis, etc.) or by treating the concentrate with an adsorbent. Adsorbents that can be used include styrene-divinylbenzene adsorbents, methacrylic acid adsorbents, hydrophilic vinyl polymers, modified dextran gel, polyacrylamide gel, reverse phase silica gel, and ion exchange resin. When an adsorbent like those is used, the fraction adsorbed on the adsorbent (hereinafter, referred to as "adsorbed fractions") contains a polyphenol compound (sulfur-containing proanthocyanidin oligomer) having a molecular weight which has been reduced by reaction with the SH group-containing compound. By Eluting the adsorbed fraction with hydroalcohol, alcohol, acetone, or the like, components that have various molecular weights can be obtained.

Measured values by normal phase HPLC and NMR confirm that the sulfur-containing proanthocyanidin oligomers thus obtained are dimers to pentamers of proanthocyanidin represented by the following general Formula (9)

(9)

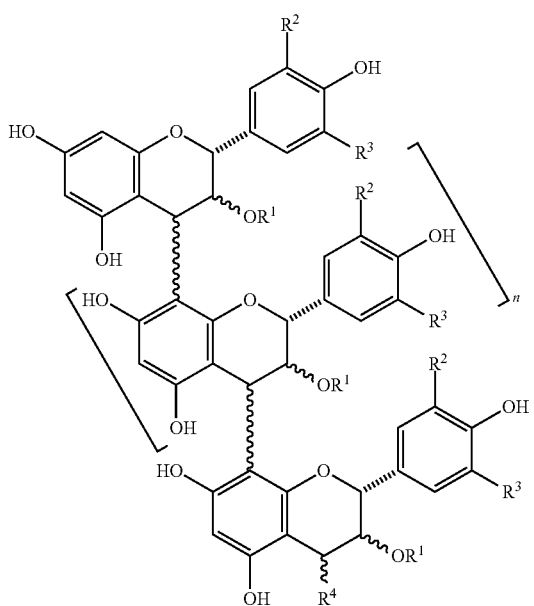

wherein n is 0 or an integer of 1 to 3, $R^1$ represents a hydrogen atom or a galloyl group represented by the following Formula,

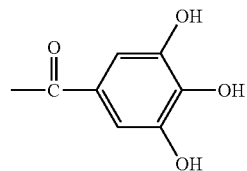

$R^2$ and $R^3$ independently represent a hydrogen atom or a hydroxyl group, and $R^4$ represents cysteine, cystine, glutathione or an SH group-containing peptide residue.

The sulfur-containing proanthocyanidin oligomer is readily absorbed into the living body through the intestine because of the molecular weight as low as 1,500 or less and exhibits a potent DPPH radical scavenging effect, SOD-like activity increasing effect, P450 lipid peroxidation preventing effect, protecting effect against FNT oxidation stress, nerve cell protecting effect against β-amyloid-induced oxidative cell death, preventing effect against Streptozotocin (STZ)-induced diabetes and so on. The oligomer has a relatively high antioxidant capacity as compared with other polyphenol materials. The data which are judged to be based on the antioxidating effects are also obtained in tests of monitoring antioxidation index on human beings.

Therefore, a composition containing the sulfur-containing proanthocyanidin oligomer of the present invention as active ingredient not only has a preventive effect against lipid peroxide production in an organism but also is effective for diseases caused by oxidation injury due to generation of active oxygen. Accordingly, the composition has preventive effects against dysfunctions of various organs and aging caused by lipid peroxides or production of active oxygen and various diseases caused by lipid peroxides or production of active oxygen are effectively treated and/or prevented by using the composition. Further, the composition is considered to be effective for the suppression, prevention, or treatment of brain dysfunctions, such as dementia, which are presumed to be caused by aging of the brain. At the same time, through the improvement in the brain function, effects of improving the learning function, alleviating distraction, relieving insomnia, recovering composedness, and so on are also expected. Therefore, the composition that contains the sulfur-containing proanthocyanidin oligomer of the present invention as an active ingredient can be utilized as a pharmaceutical composition and a health food composition.

The composition that contains the sulfur-containing proanthocyanidin oligomer of the present invention as active ingredients shows no toxicity at all and can be used quite safely. The composition is used orally or parenterally. When the composition is used orally, the dose of composition, which may vary depending on the age, body weight, symptom, target therapeutic effect, administration method and so on, is usually in the range of 100 to 2,000 mg a time for an adult. When the composition of the present invention is orally administered, generally the composition is used in the form of tablets, pills, capsules, powder, granules, syrup, and so on. When the composition of the present invention is parenterally administered, the composition is used in the form of injections, liniments and so on. When formulating the composition of the present invention into granules, tables, or syrup, appropriate auxiliary materials (starches, dextrin, sweeteners, pigments, fragrants, etc.) may be used as necessary.

BEST MODE FOR CARRYING OUT THE INVENTION

Hereinafter, the present invention will be described in more detail by way of examples and test examples of the sulfur-containing proanthocyanidin oligomer composition of the present invention. However, the present invention is not limited to the following examples.

Example 1

Production of Sulfur-Containing Proanthocyanidin Oligomer Derived from Grape Seed (1) Extraction of Grape Seed Polyphenol 8 kg of dried grape seed was extracted with 30 L of 80% methanol at room temperature for 3 days and the residue was filtered. After that, the filtrate was concentrated under reduced pressure to obtain a concentrated solution, which was purified under the following conditions.
[Purification Conditions]

The total amount of the concentrated solution was charged in DIAION HP-20 (manufactured by Mitsubishi Chemical Corporation) 200 mmφ×30 cm (about 25 L) and washed with 100 L of water. After that, an eluate obtained by using 50 L of methanol was recovered, concentrated under reduced pressure, and freeze-dried to obtain 456 g of a powdery composition.
(2) Molecular Weight Reduction Reaction with Cysteine 400 g of the grape seed polyphenol obtained in the method (1) described above, 400 g of L-cysteine (manufactured by Wako Pure Chemical Industries, Ltd.), 4 g of ascorbic acid (manufactured by Junsei Chemical Co., Ltd.), 0.8 kg of citric acid (manufactured by Wako Pure Chemical Industries, Ltd.), and 4 L of water were mixed and reacted at 40° C. for 48 hours. The reaction mixture was charged in a column (volume about 25 L) of 200 mm in diameter and 800 mm in height, packed with DIAION HP-20 (manufactured by Mitsubishi Chemical Corporation) as a carrier and a non-adsorbed fraction was washed with 100 L of water. After that, fractions eluted with 50 L of 40% ethanol were recovered, concentrated under reduced pressure, and freeze-dried to obtain reddish brown powder (yield: 408 g) that is readily soluble in water, methanol, and ethanol. The powder was fractionated with an ethanol-water mixed solution in a column (diameter: 50 mm, height: 500 mm, volume: about 1 L) packed with Sephadex LH-20 (manufactured by Pharmacia Co., Ltd.) and the oligomer composition of the fractions was analyzed by the method of Nonaka et al. (Chem. Pharm. Bull., 34(2), 633-642 (1986)). As a result, the following compositions were obtained.

| | |
|---|---|
| Cysteine-bonded epicatechin monomer fraction | 19% |
| Cysteine-bonded epicatechin dimer fraction | 21% |
| Cysteine-bonded epicatechin trimer fraction | 11% |
| Cysteine-bonded epicatechin tetramer to hexamer fraction | 16% |

(3) Cysteine-Bonded Epicatechin Monomer

The cysteine-bonded epicatechin monomer fraction thus obtained was purified by column chromatography using Sephadex LH-20 gel (water-methanol-acetone) to separate spots that had given pinkish brown when sprayed on with ninhydrin-acetic acid reagent and heated, and thereby compounds represented by the following Formulae (1) to (3) (hereinafter, sometimes abbreviated as "Compounds 1 to 3") were isolated.

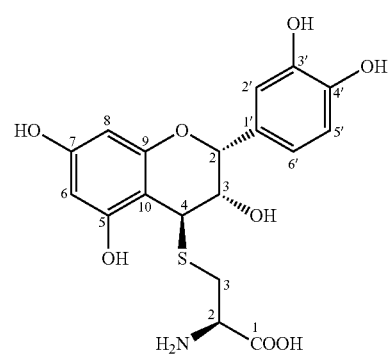

(1)

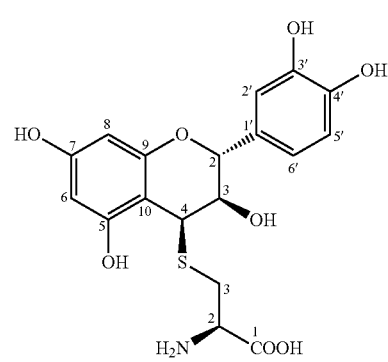

(2)

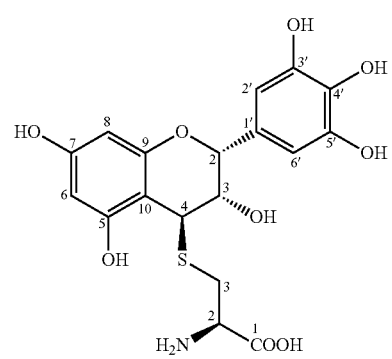

(3)

The compound of Formula (1) (Compound 1) showed a molecular ion peak $[M+H]^+$ (m/z) of 410.0925 upon measurement by HR-FAB-MS (High Resolution Fast Atom Bombardment Mass Spectroscopy), which was in agreement with a calculated value of 410.0910 corresponding to the molecular formula $C_{18}H_{20}O_8NS$ with an error of 3.6 ppm (within 10 ppm). Therefore, Compound 1 was presumed to have the molecular formula $C_{18}H_{19}O_8NS$ and its chemical structure was supposed to be such that the sulfur atom of L-cysteine was bonded to catechin or epicatechin. Further, in $^1$H-NMR (hydrogen nuclear magnetic resonance spectrum, see Table 1) measurement of Compound 1, besides the five signals of protons on an aromatic ring which are common to catechin and epicatechin, signals of structures having an oxygen atom or a sulfur atom at the base were observed at δ5.09 (br.s), δ4.07 (m), and δ3.86 (d, J=2 Hz), each amounting to one proton. The former suggests that Compound 1 has a configuration of epicatechin. The proton signal at δ3.86 (d, J=2 Hz) is assigned to a 4α arrangement corresponding to the signal of a thiolysis product in which the sulfur atom is arranged at 4β. In addition, ABX type signals were observed at δ4.13 (1H, dd, J=9, 4 Hz), δ2.95 (1H, dd, J=15, 9 Hz), and δ3.43 (1H, dd, J=15, 4 Hz), suggesting a partial structure in which a methylene group is adjacent to the methyne group in cysteine. Based on the above-mentioned information, the chemical structure of Compound 1 was presumed to be 4β-(S-L-cysteinyl)-(−)-epicatechin represented by Formula (1). Total 18 carbon signals including each carbon order observed in $^{13}$C-NMR (carbon-13 nuclear magnetic resonance spectrum, see Table 2) (DEPT method) of Compound 1 supported this structure.

In $^1$H-NMR (see Table 1) of the compound of Formula (2) (Compound 2), signals of structures having an oxygen atom or a sulfur atom at the base were observed at δ4.86 (1H, d, J=9, 6 Hz), δ4.22 (1H, dd, J=9.6, 4.3 Hz), and δ4.23 (1H, d, J=4.3 Hz), each amounting to one proton. The former two were assigned to 2β and 3β arrangements and δ4.23 (1H, d, J=4.3 Hz) was assigned to a 4α arrangement. The signals correspond to signals of a thiolysis product in which the sulfur atom is arranged at 4β. Therefore, Compound 1 and Compound 2 are considered to differ from each other only in the configuration at the 3-position, so that the chemical structure of Compound 2 was presumed to be 4β-(S-L-cysteinyl)-(+)-catechin represented by Formula (2).

The compound of Formula (3) (Compound 3) showed a molecular ion peak [M+H]$^+$ (m/z) of 426.0844 upon measurement by HR-FAB-MS, which was in agreement with a calculated value of 426.0859 corresponding to the molecular formula $C_{18}H_{20}O_9NS$ which has one more oxygen atom as compared with Compound 1 with an error of 3.5 ppm. Further, Compound 3 corresponded and was similar to Compound 1 except that in $^1$H-NMR (see Table 1) measurement of Compound 3, hydrogens at the 2'- and 6'-positions were observed as equivalent signals at δ6.57 (2H, s) in an aromatic ring region. In consideration of assignment of signals of $^{13}$C-NMR shown in Table 2, the structure of Compound 3 was presumed to be 4β-(S-L-cysteinyl)-(−)-epigallocatechin represented by Formula (3).

TABLE 1

Assignment of $^1$H-NMR signals (δ in ppm) of Compounds 1, 2, and 3

| H No. | Compound 1 | Compound 2 | Compound 3 |
|---|---|---|---|
| 2-H | 5.09 (br. s) | 4.86 (d, 2 Hz) | 5.13 (s) |
| 3-H | 4.07 (m) | 4.22 (dd, 8.3, 2 Hz) | 4.07 (s) |
| 4-H | 3.86 (d, 2 Hz) | 4.27 (d, 2 Hz) | 3.92 (s) |
| 6-H | 5.99 (d, 2 Hz) | 6.04 (d, 2 Hz) | 6.03 (br. s) |
| 8-H | 5.87 (d, 2 Hz) | 5.81 (d, 2 Hz) | 5.96 (br. s) |
| 2'-H | 6.99 (d, 2 Hz) | 6.94 (br. s) | 6.57 (s) |
| 5'-H | 6.76 (d, 8.3 Hz) | 6.86 (br. s) | |
| 6'-H | 6.81 (dd, 8.3, 2 Hz) | 6.86 (br. s) | 6.57 (s) |
| cys 2-H | 4.13 (dd, 9, 4 Hz) | 4.07 (dd, 9, 4 Hz) | 4.10 (m) |
| cys 3-H$_2$ | 2.95 (dd, 15, 9 Hz) | 3.02 (dd, 15, 9 Hz) | 3.00 (dd, 15, 9 Hz) |
| | 3.43 (dd, 15, 4 Hz) | 3.55 (dd, 15, 4 Hz) | 3.45 (dd, 15, 4 Hz) |

Notes)
Compound 1 was measured in acetone-d$_6$-D$_2$O, and Compounds 2 and 3 were measured in CD$_3$OD, respectively.

TABLE 2

Assignment of $^{13}$C-NMR signals (δ in ppm) of Compounds 1 and 3

| C No. | Compound 1 | Compound 3 |
|---|---|---|
| C-2 | 74.7 | 75.7 |
| -3 | 70.6 | 71.9 |
| -4 | 41.7 | 42.9 |
| -5 | 156.1 | 157.2 |
| -6 | 94.5 | 96.2 |
| -7 | 157.1 | 158.2 |
| -8 | 96.4 | 99.0 |
| -9 | 157.7 | 159.1 |
| -10 | 99.0 | 99.6 |
| -1' | 130.8 | 131.1 |
| -2' | 115.8 $^{a)}$ | 107.1 |
| -3' | 144.6 $^{b)}$ | 146.7 |
| -4' | 144.7 $^{b)}$ | 133.6 |
| -5' | 115.9 $^{a)}$ | 146.7 |
| -6' | 119.1 | 107.1 |
| Cys-1 | 172.1 | 172.9 |
| -2 | 53.7 | 54.7 |
| -3 | 32.9 | 34.0 |

Note 1)
Compound 1 was measured in acetone-d$_6$-D$_2$O, and Compound 3 was measured in CD$_3$OD, respectively
Note 2)
Values with $^{a)}$ and $^{b)}$ on the right in the column are interexchangeable.

(4) Cysteine-Bonded Epicatechin Dimer

Powder of cysteine-bonded epicatechin dimer fraction was purified in the same manner as above to isolate a compound represented by Formula (4) (hereinafter, sometimes abbreviated as "Compound 4").

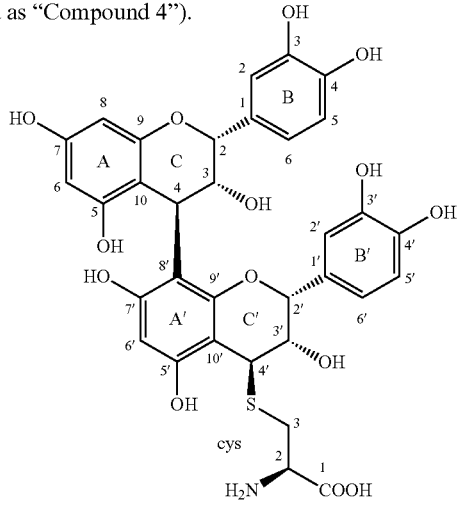

Compound 4 showed a molecular ion peak [M+H]$^+$ (m/z) of 698 upon measurement by FAB-MS, suggesting a structure that contains one more catechin unit than Compound 1. In spite of single behavior shown in TLC and HPLC, $^1$H-NMR of Compound 4 showed a spectrum in which sharp signals coexisted in broad signals. This characteristic $^1$H-NMR signal distribution suggested that out of 4→6 and 4→8, the bonding position of condensation would be the latter, which generates strong rotational hindrance. Signals derived from respective benzopyranes directly bonded to the 4→8 bond were observed to be deformed into broad. That is, δ4.22, δ4.54, and δ4.96 (each 1H, br.m, C-3, -4, and -2, respectively) were assigned to an upper end unit and sharper δ3.83 and δ3.90 (each 1H, s, c-4' and -3', respectively), 5.20 (1H, br.m, C-2') were assigned to a unit (lower end) bonded to the sulfur atom. Consideration using a molecular model suggested that the lower end unit was freer of rotational hindrance than the upper end unit. In the aromatic region at δ5.92, signals corresponding to three protons to be assigned to C-6, -8, and -6' were observed as an envelope. Protons on B rings of both units were observed from δ6.60 to δ7.09 and a sharp doublet signal having a coupling constant of 8.3 Hz among them is considered to be assigned to the 5-position in the lower end unit, which was free of rotational hindrance. The remaining signals δ2.95 and δ3.44 (each 1H, br.m, cys-C-3), and δ4.14 (1H, dd, J=9, 4 Hz, cys-C-2) were presumed to be derived from cysteine residues. $^{13}$C-NMR of Compound 4 (see Table 3), which contains signals corresponding to Compound 1, supported the structure of Compound 4 represented by Formula (4). Therefore, the structure of Compound 4 was presumed to be 4β(S-L-cysteinyl)-(−)-epicatechin-(4β→8)-(−)-epicatechin

TABLE 3

Assignment of $^{13}$C-NMR signals (δ in ppm) of Compound 4

| C No. | | C No. | |
|---|---|---|---|
| C-2 | 76.0 | C-2' | 74.6 |
| -3 | 72.0 | -3' | 69.9 |
| -4 | 36.1 | -4' | 42.0 |
| -5 | 156.6 [a] | -5' | 156.5 [a] |
| -6 | 95.3 | -6' | 95.3 |
| -7 | 156.5 | -7' | 156.6 |
| -8 | 95.3 | -8' | 99.0 |
| -9 | 156.5 | -9' | 156.6 [a] |
| -10 | 99.0 | -10' | 99.0 |
| B ring-1 | 130.7 | B ring-1' | 130.7 |
| -2 | 114.7 [b] | -2' | 115.7 |
| -3 | 144.6 [c] | -3' | 144.6 |
| -4 | 144.2 [c] | -4' | 144.2 |
| -5 | 115.0 [b] | -5' | 115.7 |
| -6 | 119.2 | -6' | 119.2 |
| | | Cys-1 | 172.2 |
| | | -2 | 53.7 |
| | | -3 | 32.8 |

Note 1) Each sample was measured in acetone-d$_6$-D$_2$O.
Note 2) Chemical shift values with [a], and [b], and [c] on the right are interexchangeable.

(5) Cysteine-Bonded Epicatechin Trimer

Powder of cysteine-bonded epicatechin monomer fraction was purified in the same manner as above to isolate a compound represented by Formula (5) (hereinafter, sometimes abbreviated as "Compound 5").

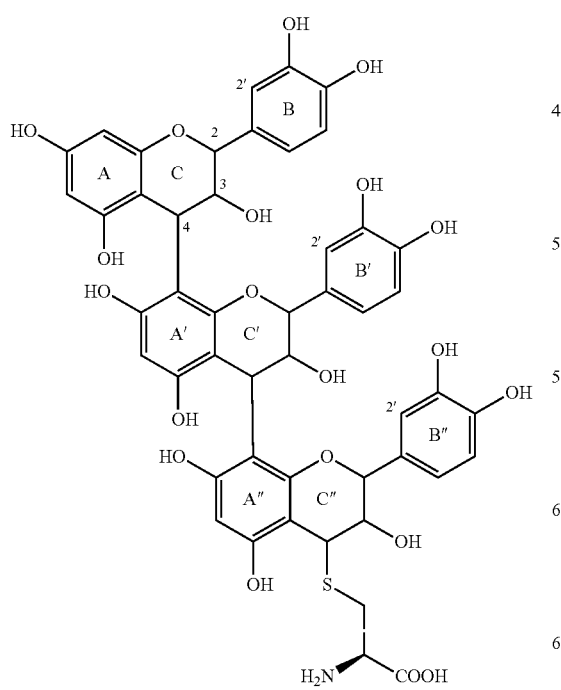

(5)

Compound 5 showed a molecular ion peak [M−H] (m/z) of 984.1956 upon measurement by HR-ESI-MS, which was in agreement with a calculated value of 984.2011 corresponding to the molecular formula $C_{48}H_{42}O_{20}NS$ with an error of 5.5 ppm. Therefore, Compound 5 was presumed to have the molecular formula $C_{48}H_{43}O_{20}NS$ and its chemical structure was supposed to be such that L-cysteine was bonded to a three-molecule condensate of catechin or epicatechin. Further, $^1$H-NMR signals of Compound 5 were generally broad and it was suggested that the three units were condensed linearly to the 4→8 bond, with L-cysteine bonded to the lower end unit. From singlets observed at δ5.98 as signals on the aromatic rings, assignment was done as follows: 6-H and 8-H on A ring, 6-H on A' ring, and 6-H on A" ring. Signals observed in lower magnetic fields (δ6.04, s; δ6.91, 7.01, s; δ7.11, s) had a peak ratio of about 3:2:1:3 and were assigned to signals derived from 2-H on B, B', and B" rings. The signals at δ6.91 and δ7.01 (2:1) were considered to have appeared as a result of signal derived from 2-H on B ring positioned in the middle of the structure was split due to rotational hindrance. Based on the information, the plane structure of Compound 5 was presumed to be of Formula (5) tentatively.

Example 2

Production of Sulfur-Containing Proanthocyanidin Oligomer Derived from Grape Seed Using the same raw material and conditions as those in Example 1, grape seed polyphenol was extracted and purified under the same conditions as those in Example 1. The purified product was reacted with glutathione under the following conditions to reduce the molecular weight.

That is, 1.0 g of the obtained grape seed polyphenol, 3.0 g of glutathione (manufactured by Wako Pure Chemical Industries, Ltd.), 0.5 g of ascorbic acid (manufactured by Junsei Chemical Co., Ltd.), and 50.0 ml of 1 N hydrochloric acid were mixed and reacted at 40° C. for 48 hours. The reaction mixture was purified by using DIAION HP-20 (manufactured by Mitsubishi Chemical Corporation), MCIgel CHP-20 (manufactured by Mitsubishi Chemical Corporation), Sephadex LH-20 (manufactured by Pharmacia Co., Ltd.) and so on, concentrated under reduced pressure, and freeze-dried to obtain reddish brown powder (yield: 120 mg).

1) Glutathione-Bonded Monomer

The obtained reddish brown powder was purified by repeating column chromatography using polystyrene gel, Sephadex LH-20 gel, and ODS silica gel as carriers, and a mixture of water and methanol as a mobile phase to obtain a compound represented by Formula (6) (Compound 6).

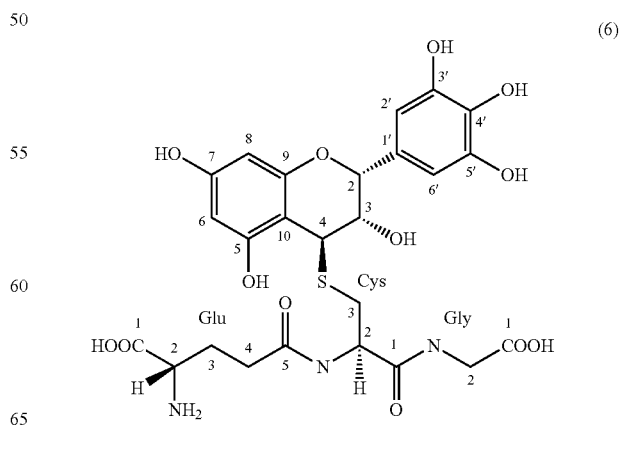

(6)

Upon measurement by HR-ESI-MS (High Resolution Electro-Spray Ionization Mass Spectroscopy), Compound 6 showed a molecular ion peak [M+H]$^+$ (m/z) of 596.1550, which was in agreement with a calculated value of 596.1551 corresponding to the molecular formula $C_{25}H_{30}O_{12}N_3S$ with an error of 0.17 ppm. Therefore, Compound 6 was presumed to have a chemical structure such that the sulfur atom derived from L-cysteine of glutathione was bonded to catechin or epicatechin. In $^1$H-NMR of Compound 6, besides 5 signals (δ5.84, 5.96, 6.91 (each 1H, 8-, 6-, 2'-H, respectively); δ6.73-6.78 (2H, m, 5'-, 6'-H)) of protons on an aromatic ring, which are common to catechin and epicatechin, signals of structures having an oxygen atom or a sulfur atom at the base were observed at δ3.90, 3.91, 5.15 (each 1H, 3-, 4-, 5-H, respectively). This suggests that a structure was such that the sulfur atom is positioned at 4β at the 4-position of epicatechin in the same manner as in Compound 1. In addition, signals corresponding to the cysteine portion (δ3.63 (1H, br.t, J=9, 4 Hz, cys-2-H), 3.72, 3.80 (each 1H, d, J=17.6 Hz, cys-3-H$_2$)), glutamic acid portion (δ1.72 (2H, m, glu-4-H$_2$), 1.78 (2H, m, glu-3-H$_2$)), 3.05 (1H, br.d, J=5.4 Hz, glu-2-H)), and glycine portion (δ3.20 (2H, s, gly-2-H$_2$)) were observed. This structure was supported by observation of 25 carbon signals in the measurement of $^{13}$C-NMR (see Table 4) of Compound 6.

Therefore, the structure of Compound 6 was presumed to be 4β-(glutathionyl)-(−)-epicatechin represented by formula (6), in which the sulfur atom derived from the cysteine portion of glutathione molecule was bonded to 4β of epicatechin.

TABLE 4

Assignment of $^{13}$C-NMR signals (δ in ppm) of Compound 6

| C No. | | C No. | |
|---|---|---|---|
| C-2 | 74.9 | glu-1 | 173.3 |
| -3 | 70.9 | -2 | 55.0 |
| -4 | 43.3 | -3 | 27.0 |
| -5 | 156.5 | -4 | 32.4 |
| -6 | 96.9 | -5 | 174.3 |
| -7 | 115.9 | cys-1 | 174.3 |
| -8 | 95.8 | -2 | 174.3 |
| -9 | 157.9 | -3 | 34.0 |
| -10 | 99.7 | gly-1 | 175.4 |
| -1' | 131.5 | -2 | 42.7 |
| -2' | 115.4 | | |
| -3' | 144.9 * | | |
| -4' | 145.0 * | | |
| -5' | 116.7 | | |
| -6' | 119.9 | | |

Note 1)
Sample was measured after being dissolved in CD$_3$OD.
Note 2)
Chemical shift values with * on the right are interexchangeable.

Example 3

Production of Sulfur-Containing Proanthocyanidin Derived from Pine Bark (1) Extraction of Pine Bark Polyphenol 400 g of Abies sachalinensis (Todo Fir) bark was extracted with 1.5 L of 80% methanol at room temperature for 3 days and the residue was filtered. After that, the filtrate was concentrated under reduced pressure to obtain a concentrated solution, which was purified under the following conditions.
[Purification Conditions]

The total amount of the concentrated solution was charged in DIAION HP-20 (manufactured by Mitsubishi Chemical Corporation) 50 mmφ×30 cm (about 600 mL) and washed with 2,500 mL of water. After that, an eluate obtained by using 1,200 mL of methanol was recovered, concentrated under reduced pressure, and freeze-dried to obtain 18.4 g of a powdery composition.

(2) Molecular Weight Reduction Reaction with Cysteine 1.0 g of the pine bark polyphenol obtained by the method (1) described above, 1.7 g of L-cysteine (manufactured by Wako Pure Chemical Industries, Ltd.), 0.25 g of ascorbic acid (manufactured by Junsei Chemical Co., Ltd.), and 20.0 mL of 1N hydrochloric acid were mixed and reacted at 40° C. for 48 hours. The reaction mixture was charged in a column (volume about 100 ml) of 25 mm in diameter and 150 mm in height, packed with DIAION HP-20 (manufactured by Mitsubishi Chemical Corporation) as a carrier and a non-adsorbed fraction was washed with 400 mL of water. After that, fractions eluted with 400 mL of methanol were recovered, concentrated under reduced pressure, and freeze-dried to obtain reddish brown powder (yield: 0.95 g).

Proanthocyanidin exhibits strong antioxidation activity in vitro while proanthocyanidin does not always exhibit a sufficient effect in vivo by oral intake. Presumably the reason is that high molecular weight proanthocyanidin cannot readily be absorbed from the intestine. In contrast, the sulfur-containing proanthocyanidin oligomer having a molecular weight reduced by using the SH group-containing substance according to the present invention exhibits antioxidation activity equivalent to that of high molecular weight proanthocyanidin in vitro and also exhibit antioxidation activity superior to that of the high molecular weight proanthocyanidin in vivo.

Example 4

Production of Sulfur-Containing Proanthocyanidin Derived from Myrica Rubra (1) Extraction of Myrica Rubra Polyphenol 400 g of Myrica rubra (bayberry) bark was extracted with 1.5 L of 80% methanol at room temperature for 3 days and the residue was filtered. After that, the filtrate was concentrated under reduced pressure to obtain a concentrated solution, which was purified under the following conditions.
[Purification Conditions]

The total amount of the concentrated solution was charged in DIAION HP-20 (manufactured by Mitsubishi Chemical Corporation) 50 mmφ×30 cm (about 600 mL) and non-adsorbed fractions were washed with 2,500 mL of water. After that, an eluate obtained by using 1,200 mL of methanol was recovered, concentrated under reduced pressure, and freeze-dried to obtain 38.0 g of a powdery composition.

(2) Molecular Weight Reduction Reaction with Cysteine 1.0 g of the Myrica rubra polyphenol obtained by the method (1) described above, 1.7 g of L-cysteine (manufactured by Wako Pure Chemical Industries, Ltd.), 0.25 g of ascorbic acid (manufactured by Junsei Chemical Co., Ltd.), and 20.0 mL of 1N hydrochloric acid were mixed and reacted at 40° C. for 48 hours. The reaction mixture was charged in DIAION HP-20 (manufactured by Mitsubishi Chemical Corporation) of 25 mmΦ in diameter and 150 mm in height (volume about 100 mL) and a non-adsorbed fraction was washed with 400 mL of water. After that, an eluate obtained by using 400 mL of methanol was recovered, concentrated under reduced pressure, and freeze-dried to obtain 0.95 g of reddish brown powder.

(3) Regarding Combination of Bayberry Bark Polyphenol and L-Cysteine
1) L-Cysteine-Bonded Epigallocatechin Gallate Monomer The reddish brown powder obtained in (2) described above was purified by repeating column chromatography using polystyrene gel, Sephadex LH-20 gel, and ODS silica gel as carriers, and a mixture of water, methanol, and acetone in optional ratios as a mobile phase to isolate epicatechin gallate, epigallocatechin gallate, (4β→8) epigallocatechin gallate, and the above-mentioned Compound 3 as well as the following compounds represented by Formulae (7) and (8) (Compound 7 and Compound 8).

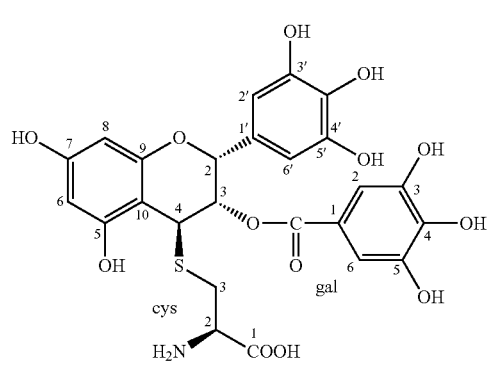

(7)

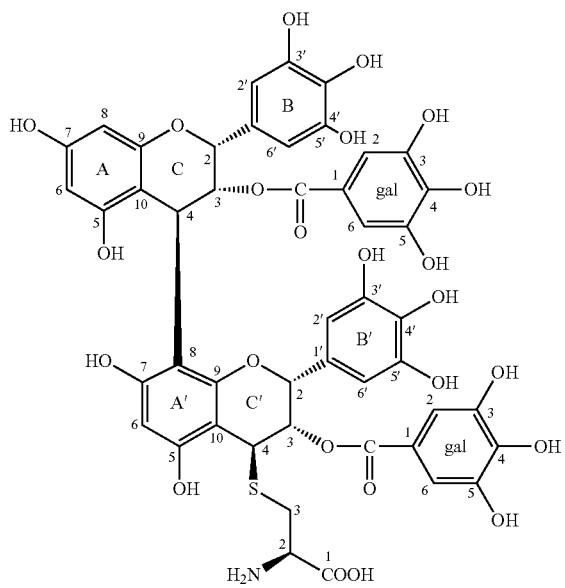

(8)

Compound 7 showed a molecular ion peak [H–H]+ (m/z) of 575 upon measurement by ESI-MS. Further, results of measurement by $^1$H-NMR (see Table 5) indicated that compound 7 was similar to Compound 1 and Compound 3. However, there were observed 3-βH (1H, 5.29, s) which was shifted toward lower magnetic fields by about 1.3 ppm, as well as 6- and 8-positions on ring A in an aromatic ring region, and two sets of sharp, equivalent singlet signals (derived from the 2- and 6-position hydrogens on 1,3,4,5-substituted benzene) each amounting to two protons. Those signals suggested that Compound 7 is a gallate of epigallocatechin.

Taking into consideration the information and assignment of $^{13}$C-NMR signals together, the structure of Compound 7 was presumed to be 4β-(S-L-cysteinyl)-(–)-epicatechin gallate represented by Formula (7).

2) L-Cysteine-Bonded Epigallocatechin Gallate Dimer

Upon measurement by HR-ESI-MS, Compound 8 showed a molecular ion peak [M–H]+ (m/z) of 1032.1517, which was in agreement with a calculated value of 1032.1503 corresponding to the molecular formula $C_{25}H_{30}O_{12}N_3S$ with an error of 1.4 ppm. Therefore, Compound 8 was presumed to have a structure having one more epicatechin gallate unit than Compound 7. $^1$H-NMR of Compound 8 showed a spectrum in which a sharp signal coexisted in broad signals similarly to Compound 4, and was considered to be of 4→8 condensation type. Signals of $^1$H- and $^{13}$C-NMR were assigned similarly to Compound 4 (Tables 5 and 6, respectively) and the structure of Compound 8 was presumed to be 4β-(S-L-cysteinyl)-(–)-epicatechin gallate-(4β→8)-(–)-epicatechin gallate represented by Formula (8).

TABLE 5

Assignment of $^1$H-NMR signals (δ in ppm) of Compounds 7 and 8

| H No. | Compound 7 | Compound 8 |
|---|---|---|
| C-2-H | 5.37 (s) | 5.50 (s) |
| 3-H | 5.29 (s) | 4.75 (s) |
| 4-H | 4.16 (s) | 4.15 (br. s) |
| A-6-H | 6.08 (s) | 5.87 (br. s) |
| 8-H | 6.01 (d, 2.2 Hz) | 5.90 (br. s) |
| B-2'-H | 6.45 (s) | 6.45 (br. s) |
| 6'-H | 6.45 (s) | 6.45 (br. s) |
| gal-2-H | 6.96 (s) | 6.96 (br. s) |
| gal-6-H | 6.96 (s) | 7.00 (br. s) |
| C'-2-H | | 5.39 (br. s) |
| 3-H | | 5.12 (br) |
| 4-H | | 4.15 (br. s) |
| A'-6-H | | 6.09 (br. s) |
| 8-H | | — |
| B'-2'-H | | 6.57 (br. s) |
| 6'-H | | 6.57 (br. s) |
| gal-2-H | | 7.00 (br. s) |
| gal-6-H | | 7.00 (br. s) |
| cys 2-H | 4.19 (br. m) | 4.07 (dd, 9, 4 Hz) |
| cys 3-H$_2$ | 3.17 (dd, 15, 8 Hz) | 3.02 (dd, 15, 9 Hz) |
| | 3.71 (br. d, 15 Hz) | 3.55 (dd, 15, 4 Hz) |

Notes)
Compound 7 was measured at 25° C., Compound 8 was measured at 40° C. in acetone-d$_6$-D$_2$O.

TABLE 6

Assignment of $^{13}$C-NMR signals (δ in ppm) of Compounds 7 and 8

| C No. | Compound 7 | | Compound 8 | | |
|---|---|---|---|---|---|
| C-2 | 74.0 | C-C-2 | 75.0 | C'-C-2 | 73.5 |
| -3 | 74.0 | -3 | 75.0 | -3 | 73.5 |
| -4 | 39.3 | -4 | 32.4 | -4 | 38.9 |
| -5 | 156.2 | A-C-5 | 154.8 | A'-C-5 | 154.8 |
| -6 | 95.4 | -6 | 94.7 | -6 | 94.7 |
| -7 | 157.3 | -7 | 156.1$^{a)}$ | -7 | 155.9$^{a)}$ |

TABLE 6-continued

Assignment of $^{13}$C-NMR signals (δ in ppm) of Compounds 7 and 8

| C No. | Compound 7 | | Compound 8 | | |
|---|---|---|---|---|---|
| -8 | 97.0 | -8 | 95.3 | -8 | 95.3 |
| -9 | 158.9 | -9 | 156.5 | -9 | 156.5 |
| -10 | 97.9 | -10 | 96.6 | -10 | 96.9 |
| -1' | 129.3 | B-C-1 | 131.9 | B'-C-1 | 131.9 |
| -2' | 106.4 | -2 | 106.0 | -2 | 106.0 |
| -3' | 145.6 | -3 | 131.9 | -3 | 131.9 |
| -4' | 132.9 | -4 | 119.6 | -4 | 119.6 |
| -5' | 145.6 | -5 | 144.8 | -5 | 144.8 |
| -6' | 106.4 | -6 | 106.0 | -6 | 106.0 |
| gal-C-1 | 120.2 | gal-C-1 | 119.6 | gal-C-1 | 119.6 |
| -2 | 109.8 | -2 | 109.4[a] | -2 | 109.4 |
| -3 | 146.0 | -3 | 145.0 | -3 | 145.3 |
| -4 | 139.2 | -4 | 138.8 | -4 | 138.8 |
| -5 | 146.0 | -5 | 145.0 | -5 | 145.3 |
| -6 | 109.8 | -6 | 109.5[b] | -6 | 109.4 |
| —C(=O)O— | 167.0 | —C(=O)O— | 166.7 | —C(=O)O— | 166.7 |
| Cys-1 | 171.8 | | | Cys-1 | 171.0 |
| -2 | 53.9 | | | -2 | 53.3 |
| -3 | 33.3 | | | -3 | 32.6 |

Note 1)
Compound 1 was measured in acetone-$d_6$-$D_2O$, Compound 3 was measured in $CD_3OD$.
Note 2)
Chemical shift values with [a] and [b] on the right are interexchangeable.

Test Example 1

DPPH Radical Scavenging Effect

The powder before fractionation of Example 1 (Substance 1), monomer fraction (Substance 2) obtained by fractionating Substance 1, dimer and trimer fractions (Substance 3) obtained by fractionating Substance 1, tetramer to hexamer fractions (Substance 4) obtained by fractionating Substance 1, raw material in Example 1 (grape seed polyphenol extract) (Comparative Substance 1), and commercially available catechin (manufactured by Wako Pure Chemical Industries, Ltd.) (Comparative Substance 2) were measured for 1,1-diphenyl-2-picrylhydrazyl (DPPH) radical scavenging effect by the following method.

100 μl of a DPPH solution (60 μM ethanol solution) was charged in a 96-well microplate and 100 μl of an ethanol solution as a test sample or 100 μl of ethanol as a control was added, and the whole was gently mixed and left to stand at room temperature for 30 minutes. Then, absorbance at 520 nm was measured and a DPPH radical scavenging ability was calculated according to the following formula. 50% effective concentration ($EC_{50}$) was calculated from the DPPH radical scavenging ability and concentrations of gradually diluted test samples.

DPPH radical scavenging ability(%)[(1−(absorbance of test sample))/(absorbance of control)]×100

50% effective concentration ($EC_{50}$) was calculated from DPPH radial scavenging abilities in gradual concentrations of each sample. Table 7 shows the results.

At low concentrations, Substance 4 had a relatively high DPPH radical scavenging ability. Other samples showed similar activities. At high concentrations, each sample showed high activity.

TABLE 7

| $EC_{50}$ in DPPH radical scavenging $EC_{50}$ |  |
|---|---|
|  | (μg/mL) |
| Substance 1 | 1.62 |
| Substance 2 | 2.78 |
| Substance 3 | 1.45 |
| Substance 4 | 0.77 |
| Comparative Substance 1 | 1.55 |
| Comparative Substance 2 | 1.71 |

Test Example 2

Superoxide Dismutase (SOD)-Like Activity

With respect to Substances 1 to 4 and Comparative Substances 1 and 2 which were the same as those used in Test Example 1, SOD-like activity was measured using a blood SOD activity measuring kit (SOD Test Wako: manufactured by Wako Pure Chemical Industries, Ltd.). SOD-like activity was calculated according to the following formula and 50% effective concentration ($EC_{50}$) was calculated based on the relationship with the concentration of test sample.

SOD-like activity(%)=[(1−(absorbance of test sample))/(absorbance of control)]×100

$EC_{50}$ was calculated from SOD-like activities in gradual concentrations of each sample. Table 8 shows the results. Each fraction of Substances 2 to 4 showed high SOD-like activity as compared with Comparative Substances 1 and 2.

TABLE 8

| $EC_{50}$ in SOD-like activity |  |
|---|---|
|  | (μg/mL) |
| Substance 1 | 69.7 |
| Substance 2 | 84.8 |

TABLE 8-continued

EC$_{50}$ in SOD-like activity

|  | (μg/mL) |
| --- | --- |
| Substance 3 | 74.6 |
| Substance 4 | 75.5 |
| Comparative Substance 1 | 70.9 |
| Comparative Substance 2 | 62.0 |

Test Example 3

Effect on Subacute FeNTA-Induced Multiple Organ Failure Model

Tests were carried out using FeNTA (a mixture of iron nitrate (Fe(NO$_3$)$_3$) and sodium nitrilotriacetate (NTA$_3$Na)) known as an in vivo oxidation model that generates a large amount of active oxygen when administered in an organism to induce multiple organ failure.

That is, a solution of 240 mg of iron nitrate nonahydrate (manufactured by Kanto Kagaku) in 40 ml of cold water and a solution of 390 mg of sodium nitrilotriacetate monohydrate in 40 ml of cold water were mixed under ice cooling and the mixture was adjusted to pH 7.5 with 1N hydrochloric acid and also adjusted to a fixed volume of 100 mL to make an FeNTA solution. Within 10 minutes after the preparation, 22.5 mg/kg body weight as Fe of the FeNTA solution was intraperitoneally administered to male ddY mice of 7 weeks in age (average body weight of 30 g) every other day. Substance 1 and Comparative Substance 1 were each forcibly orally administered every day in a dose of 25 mg/kg body weight (low dose-administered group) or 50 mg/kg body weight (high dose-administered group). Control group was caused to take city water. Negative control group to which no FeNTA was administered and positive control group to which FeNTA was administered were prepared. The animals were allowed to freely take drinking water and feed. Blood was collected on day 7, 14, 21, and 28 from the start of the administration. The serum lipid peroxide (LPO) level was measured. On day 28 from the start of the administration, the animals were dissected to remove liver, kidney, and brain, and the LPO level of homogenate of each organ was measured.

Figure 2:
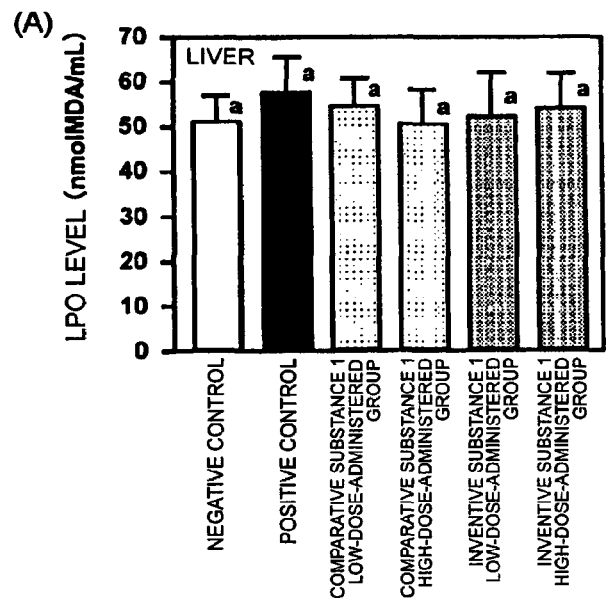
FIGS. 2A, 2B, and 2C are graphs illustrating LPO levels in (FIG. 2A) livers, (FIG. 2B) kidneys, and (FIG. 2C) brains of mice administered with the sulfur-containing proanthocyanidin oligomer composition according to Example 1 of the present invention (Substance 1) and its raw material (Comparative Substance 1), respectively.
Figure 2:
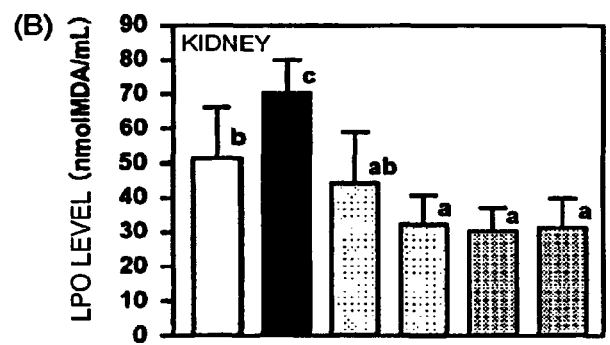
Figure 2:
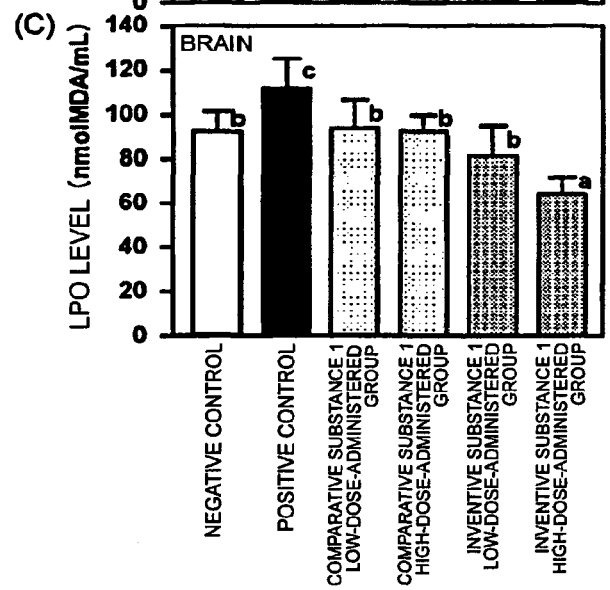

[Test Results]
(1) FIGS. 1(A) and 1(B) show serum LPO levels. In the low dose-administered group, the serum LPO level of Substance 1 group was decreased significantly as compared to Comparative Substance 1 group and positive control group on Day 21 (FIG. 1(A)). Also in high dose-administered group, the serum LPO level of Substance 1 group was decreased significantly on day 21 from the start of the administration and subsequently (FIG. 1(B)). Comparative Substance 1 group also showed a low level on day 21 but the substance of the present invention showed higher effects.
(2) LPO Level in Each Organ
FIGS. 2A to 2C show LPO levels in liver, kidney, and brain.
In liver, no significant increase in LPO level by the administration of FeNTA was observed or no change in each administered group was observed. In kidney and brain, the administration of FeNTA increased the LPO level in the homogenate. Administration of Substance 1 and Comparative Substance 1 decreased the LPO level. Both kidney and brain showed the lowest level in Substance 1-high dose-administered group. In particular, in brain, administration of Comparative Substance 1 also showed low levels. However, Substance 1-high dose-administered group showed significantly low levels as compared with the other groups.

[Summary of the Results]
Administration of FeNTA increased the serum LPO level. Substance 1 exhibited the effect in low doses and in short periods as compared with Comparative Substance 1. This shows that because of reduction in molecular weight, Substance 1 is more readily absorbed by the intestine when orally taken, so that Substance 1 exhibits the effect in low doses and in short periods. In particular, it has been clarified that Substance 1 exhibits potent antioxidation activity in kidney and brain.

Test Example 4

Monitoring Test on Human Beings

[Test Method]
Thirty four (34) healthy persons (average age: 41.2 years old, 21 males and 13 females) were divided into two groups as shown in Table 9, and 500 mg/day of each of Substance 1 and Comparative Substance 1 was administered for 28 days. Blood was collected before start of the administration and after 28 days from the administration, and the serum LPO level and SOD-like activity were measured.

TABLE 9

| Administered Group | Average Age | Male/female ratio | LPO initial level High | SOD initial level low |
| --- | --- | --- | --- | --- |
| Substance 1 | 41.9 years old | 10 males 6 females | 7 persons | 7 persons |
| Comparative Substance 1 | 40.5 years old | 11 males 6 females | 11 persons | 8 persons |

Figure 3:
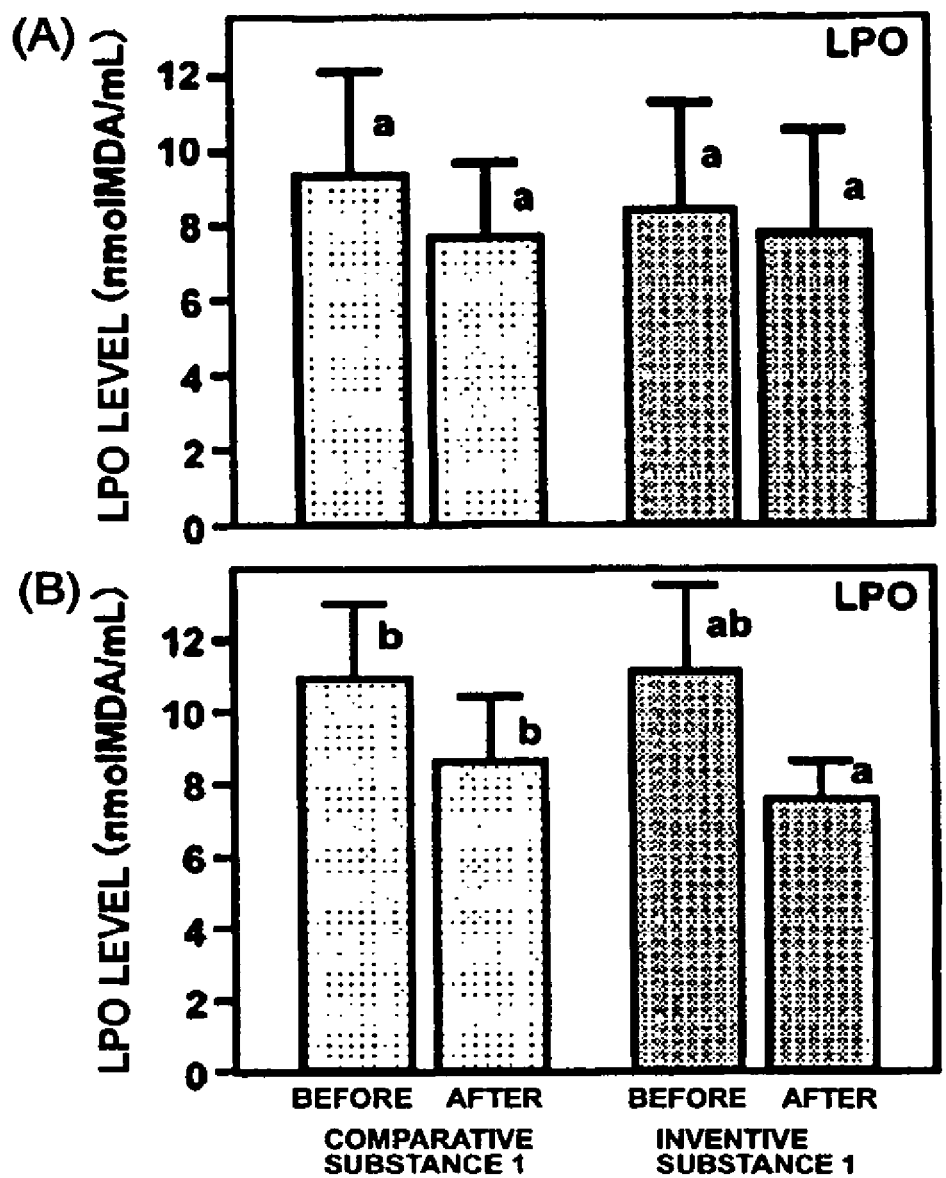
FIG. 3A relates to persons whose initial values in LPO levels were normal, and FIG. 3B relates to persons whose initial values in LPO levels were abnormal, both of which illustrate serum LPO levels in human beings administered with the inventive composition according to Example 1 (Substance 1) and the raw material according to Example (Comparative Substance 1).
Figure 4:
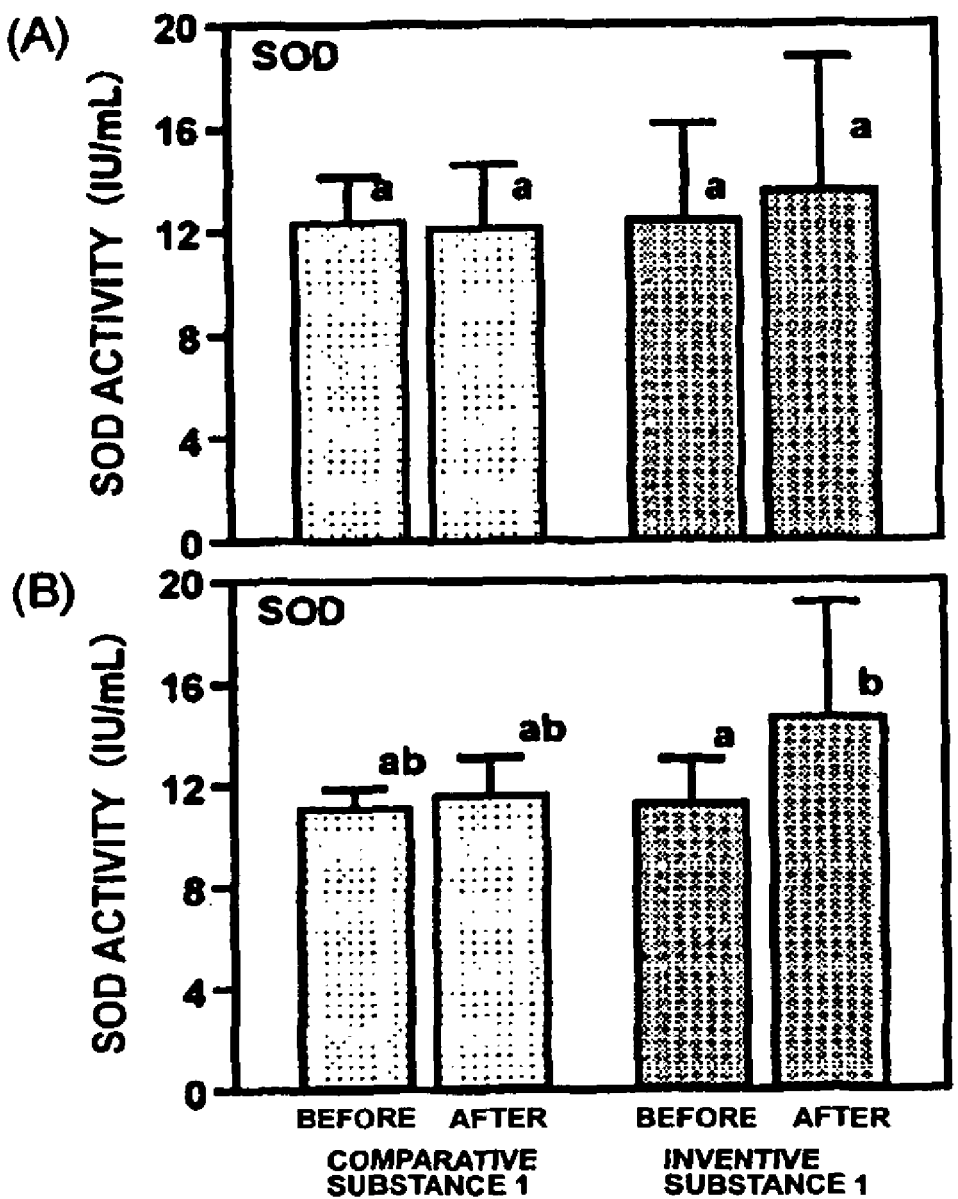
FIG. 4A relates to persons whose initial values in SOD levels were normal, and FIG. 4B relates to persons whose initial values in SOD levels were abnormal, both of which illustrate serum SOD levels in human beings administered with the inventive composition according to Example 1 (Substance 1) and the raw material according to Example (Comparative Substance 1).

[Results]
FIGS. 3A, 3B, 4A, and 4B show the LPO level and SOD-like activity before and after the administration. FIG. 3A shows LPO levels for persons with normal initial levels and FIG. 3B shows LPO levels for persons with abnormal initial levels. FIG. 4A shows SOD-like activity for persons with normal initial values and FIG. 4B shows SOD-like activity for persons with abnormal initial values.

By administration of Comparative Substance 1 and Substance 1 for 28 days, LPO levels showed a decrease and SOD-like activity showed a tendency to increase. Among subjects with abnormal initial levels, those with a relatively high initial LPO level (LPO level of 8.0 or more) and those with a relatively low SOD-like activity (SOD-like activity of 12.0 or less), statistically significant decrease in the LPO level was observed in a group administered with Substance 1 (FIG. 3(B)). Similarly, statistically significant increase in SOD-like activity was observed in a group administered with Substance 1 (FIG. 4(B)). This confirmed that Substance 1 is more effective to improve an oxidation state of an organism than the same amount of Comparative Substance 1.

Test Example 5

Effect of Protecting Nerve Cell from Oxidative Cell Death Induced by β-Amyloid

Alzheimer's disease, which is caused by abnormal regeneration of nerve, is characterized in that the disease forms senile plaque by accumulation of (β-amyloid. β-Amyloid is a substance that generates active oxygen species and that plays a key role in the onset and progress of Alzheimer's disease due to cytotoxicity to nerve cells. Molecular weight-reduced polyphenol (hereinafter, sometimes abbreviated as "GSM") was examined for nerve cell protecting effect against cell injuring activity by apoptosis induction on PC-12 cells widely used in experiments of nervous cytotoxicity.

[Test Method]

PC-12 cells were cultivated in DMEM medium containing 10% heat-inactivated equine serum and 5% fetal bovine serum in an atmosphere of 10% carbon dioxide. After precultivation for 24 hours with adjusting the cell density to $4 \times 10^4$ cells/300 μL, GSM or grape seed polyphenol (hereinafter, sometimes abbreviated as "GSP") was added to N-2 medium containing no serum in a concentration of 1, 1.5, 5, or 10 μg/mL and cultivation was performed on a 48-well plate.

(1) Cell Survival Test:

After treatment, the cells were treated with a 1 mg/mL MTT solution and a deep blue formazan product was dissolved in a buffer and measured of absorbance at 540 to 595 nm. The results are shown in a ratio (%) to absorbance of non-treated control cell.

[Results]

Figure 5:
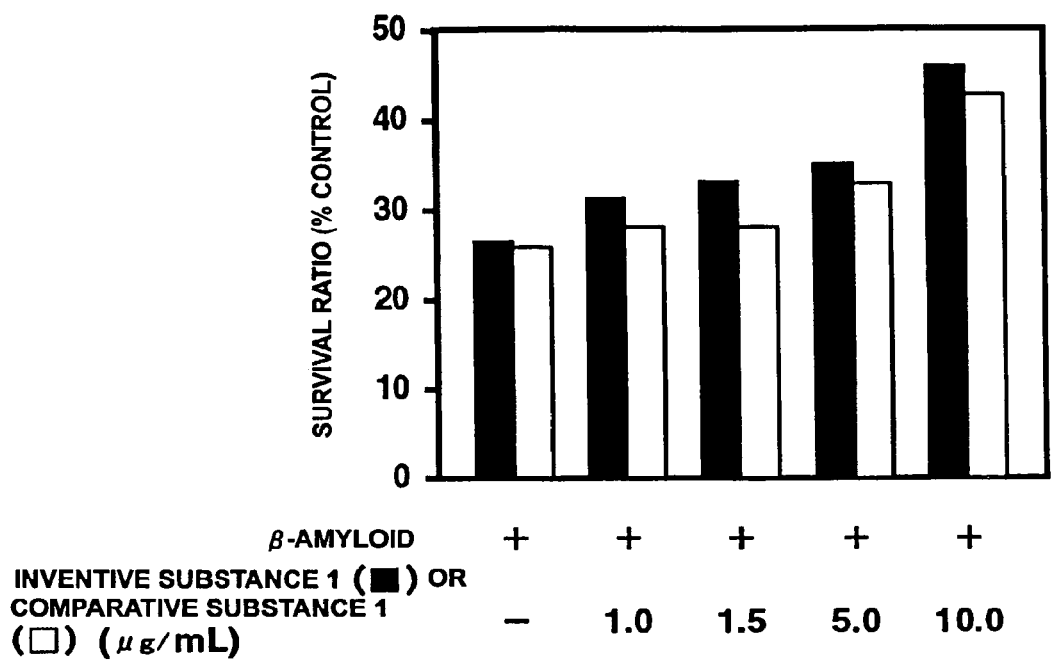
FIG. 5 is a graph illustrating effects of inhibiting PC-12 cell death, with respect to β-amyloids in inventive Substance 1 and Comparative Substance 1 according to Example 1.

The MTT test proved that GSM concentration-dependently suppressed PC-12 cell death due to β-amyloid. Its effect was higher than GSP in a low concentration region of particularly 1 and 1.5 μg/mL (FIG. 5).

(2) Mitochondrial Membrane Potential Measurement Test:

TMRE, a fat-soluble cation probe, was used for measuring mitochondrial membrane potential. PC-12 Cells ($1 \times 10^4$ cell/mL) were treated with 25 μM β-amyloid in the presence/absence of GSM or GSP and then washed with phosphate buffer saline, followed by treatment with TMRE (150 nM) at 37° C. for 30 minutes. TRME that was accumulated depending on the membrane potential of mitochondria was detected by using fluorescence at an excitation wavelength of 488 nm and an emission wavelength of 590 nm.

[Results]

Figure 6:
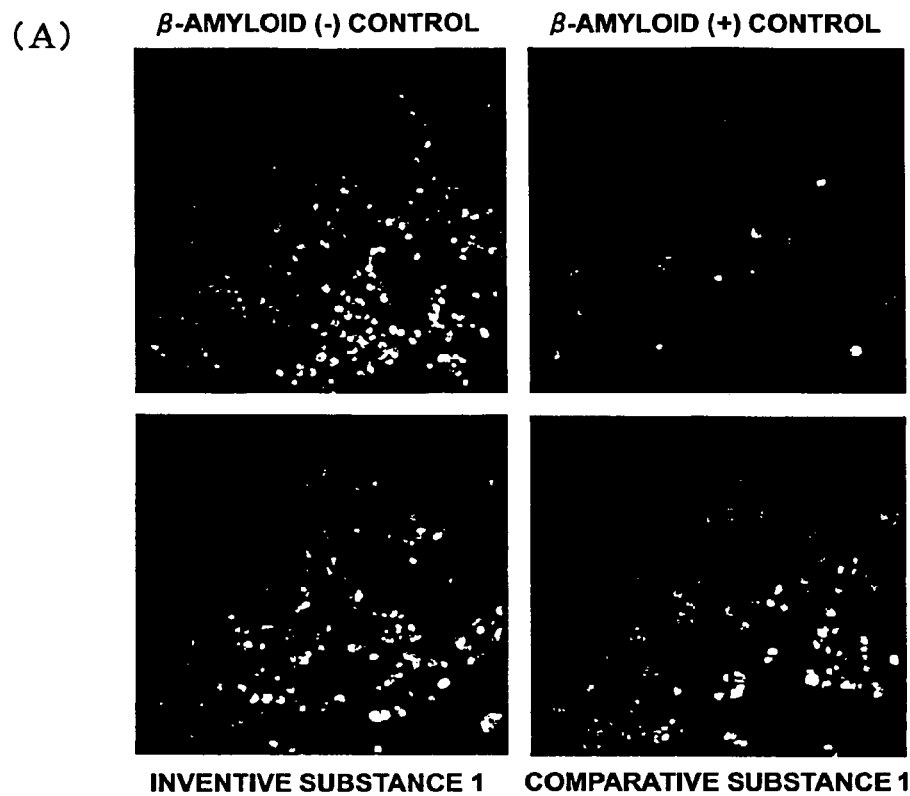
FIGS. 6A and 6B are a photograph and a graph, respectively, showing effects of inhibiting decrease in mitochondrial membrane potential, with respect to β-amyloids in Substance 1 and Comparative Substance 1 according to Example 1.
Figure 6:
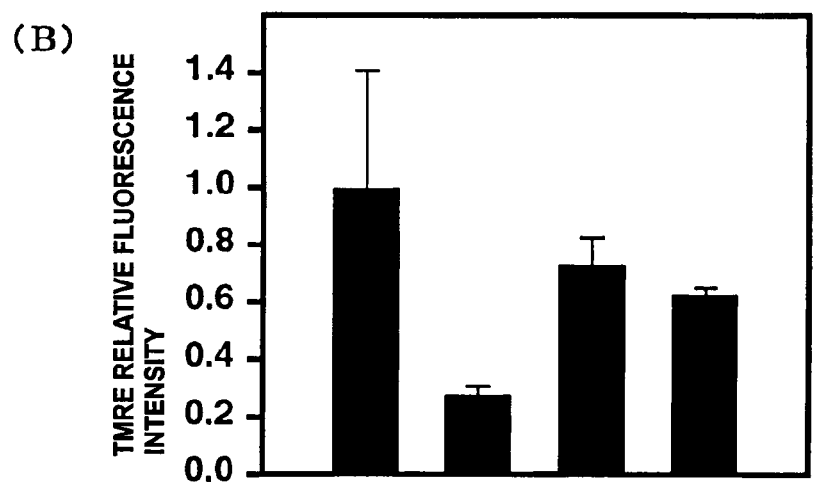

Mitochondria undergoes alteration in the integrity of the membrane prior to symptom of cell death. This change occurs in both inner and outer membranes of mitochondria, finally leading to discharging of transmembrane potential to release a soluble intermembraneous protein such as cytochrome C and a change in membrane permeability. When exposed to β-amyloid, PC-12 cells undergo a rapid decrease in mitochondria transmembrane potential, which is expressed by red fluorescence using TMRE, which is a potential-dependent dye (FIG. 6(A)). The decrease in transmembrane potential by β-amyloid is significantly suppressed by pretreatment with GSM and the effect was higher than that of GSP (FIGS. 6(A) and 6(B)).

(3) Measurement of Accumulation of Active Oxygen Species in Cell:

To observe the accumulated amount of active oxygen species in cell, fluorescent probe DCF-DA (2',7'-dichlorodihydrofluorescein-diacetate) was used.

After PC-12 cells ($1 \times 10^6$ cell/3 mL) are treated with 25 μM β-amyloid in the presence/absence of GSM or GSP, the cells were washed with Krebs-Ringer solution and 10 μM DCF-DA was added thereto. After cultivation at 37° C. for 15 minutes, the cells were observed by using a confocal laser microscope equipped with argon laser at an excitation wavelength of 488 nm and an emission wavelength of 530 nm.

[Results]

Figure 7:
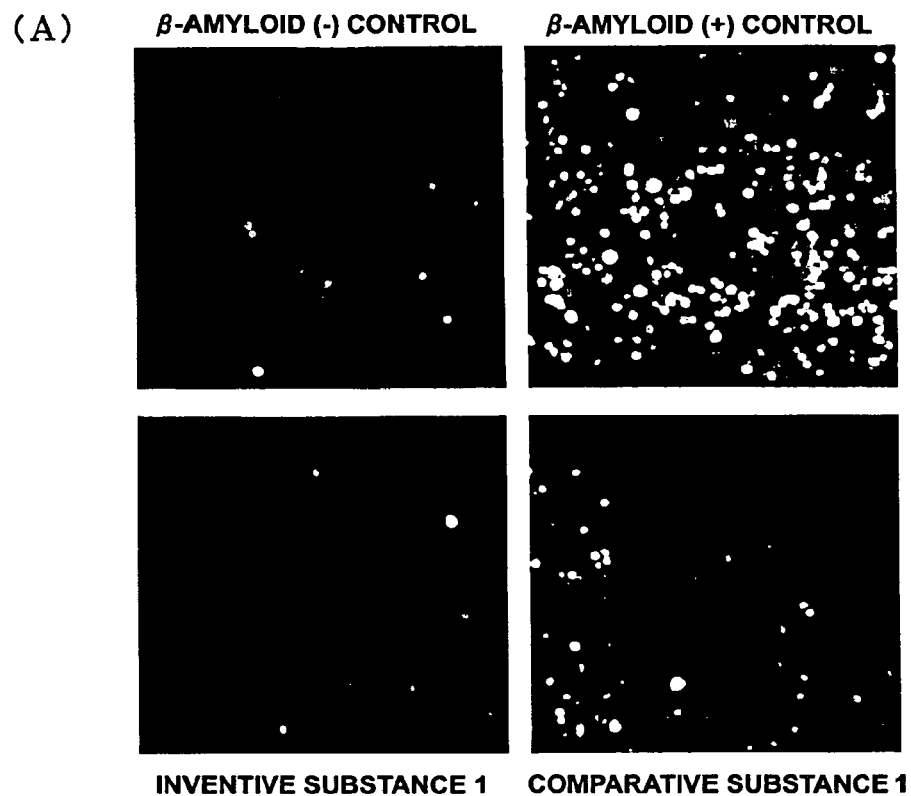
FIGS. 7A and 7B are a photograph and a graph, respectively, showing effects of reducing accumulation of active oxygen species in PC-12 cells, with respect to β-amyloids in Inventive Substance 1 and Comparative Substance 1.
Figure 7:
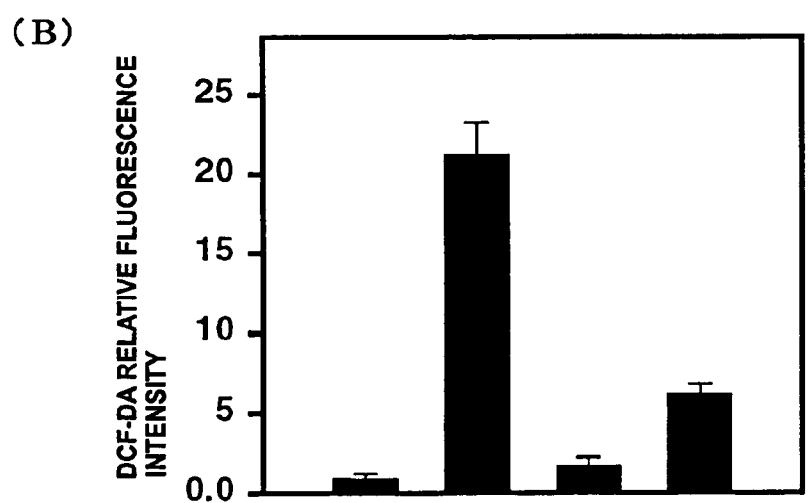

To elucidate oxidation stress in cell death of PC-12 cell due to β-amyloid, intracellular accumulation of active oxygen species was measured by using DCF-DA that can permeate through a cell membrane. In a cell, DCF-DA is hydrolyzed to DCF because of the esterase activity of the cell and reacts with a peroxide to produce a fluorescent substance. PC-12 cells treated with β-amyloid are stained with a DCF dye and displayed (FIG. 7(A)). The accumulation of active oxygen species in cell due to β-amyloid was decreased by GSM and the reduction effect was higher than GSP (FIGS. 7(A) and 7(B)).

(4) Intracellular Glutathione Level

The intracellular glutathione level was measured by using a commercially available kit (BIOXYTECH GSH-400: manufactured by OXIS Research Corporation, U.S.A.). β-Amyloid-treated PC-12 cells cultivated in the presence/absence of GSM or GSP were recovered and homogenized in a metaphosphoric acid solution, and were centrifuged to obtain a supernatant, to which was added a chromogen hydrochloric acid solution. After stirring, a 30% sodium hydroxide solution was added and the cells were cultivated at 25° C. for 10 minutes and then centrifuged to obtain a transparent supernatant, which was measured for absorbance at 400 nm. The protein content was measured by using a BCA protein measuring kit and concentration of glutathione of the protein per unit weight of the protein was compared with that of non-treated control.

[Results]

Figure 8:
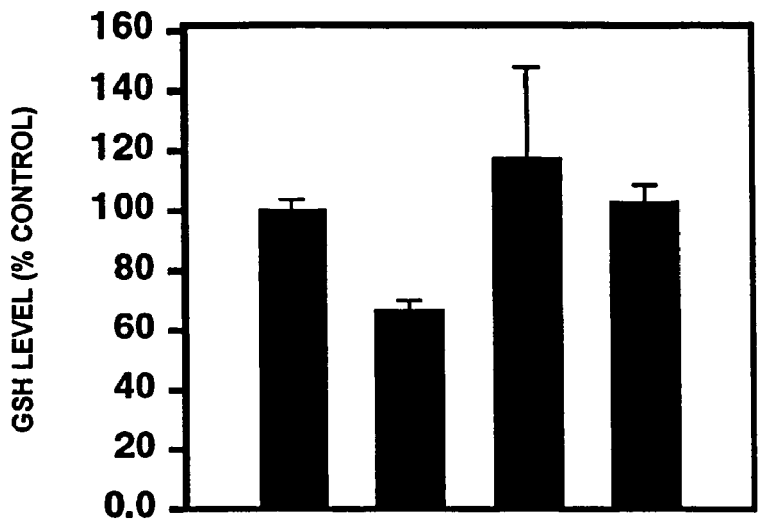
FIG. 8 is a graph illustrating intracellular antioxidative effects of β-amyloids in Inventive Substance 1 and Comparative Substance 1.

Oxidation damage is involved in the cell death due to β-amyloid. In cells treated with β-amyloid, the intracellular glutathione level was decreased. In GSP-treated cells, the intracellular glutathione level was recovered to a normal level while in the case of GSM, an intracellular glutathione level above the normal level was shown, so that GSM exhibited high antioxidation activity in the cell (FIG. 8).

(5) Lipid Peroxide Level:

The lipid peroxide level was measured by using a commercially available kit (BIOXYTECH LPO-586: manufactured by OXIS Research Corporation, U.S.A.). β-Amyloid-treated PC-12 cells cultivated in the presence/absence of GSM or GSP were recovered and homogenized in a 20 mM Tris-hydrochloride buffer containing 0.5 mM butylated hydroxytoluene, and were centrifuged to obtain a supernatant, which was diluted and mixed with an acetonitrile solution of 10.3 mM N-methyl-2-phenylindole. After 37% hydrochloric acid had been added, the mixture was cultivated at 45° C. for 60 minutes. After cooling, centrifugation was performed to obtain a transparent supernatant, which was measured for absorbance at 590 nm. The protein content was measured by using a BCA protein measuring kit and concentration of lipid peroxide of the protein per unit weight of the protein was compared with that of non-treated control.

[Results]

Figure 9:
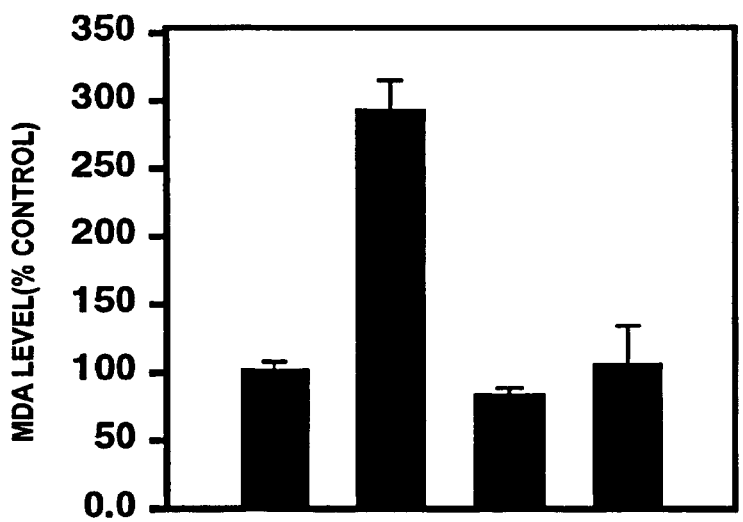
FIG. 9 is a graph illustrating inhibitory effects of inhibiting transmembrane oxidation with respect to β-amyloids in Inventive Substance 1 and Comparative Substance 1.

Peroxidation of a cell membrane caused by treatment with β-amyloid is indicated by malonedialdehyde (MDA) produced from a lipid peroxide. Pretreatment with GSM or GSP suppressed peroxidation of lipid by β-amyloid and the effect of GSM was the higher, suppressing lipid peroxide to the level of non-treated control or less (FIG. 9).

[Summary of Results]

GSM suppressed cell death of nerve cells due to β-amyloid toxicity by decreasing the accumulation of active oxygen species in nerve cells in PC-12 cells, which are model cell line of nerve cell. The effect was higher than that of GSP. While oxidation damage to cells is involved in the cell death of nerve cells due to β-amyloid toxicity, GSM suppressed oxidation damage to cells and the effect of GSM was higher than that of GSP.

Suppression of cell death of nerve cells due to (β-amyloid that is deeply involved in the onset and progress of Alzheimer's by GSM by virtue of antioxidation effect indicates that the onset and progress of Alzheimer's disease can be suppressed with GSM.

Test Example 6

Preventive Effect Against Streptozotocin (STZ)-Induced Diabetes

In order to examine the preventive effect of Substance 1 against STZ-induced diabetes mice, a clinical condition model corresponding to an initial stage of diabetes induced by administering STZ in a multiple low dose (MLD) was used.
[Method]
Jla:ddy mice (male, 7 weeks in age) were measured for body weight, blood glucose level, and blood LPO level and were grouped as follows so that each group was equalized.
(1) Negative control group: STZ(−) (n=5, 1 cage),
(2) Positive control group: STZ(+) (n=15, 3 cages),
(3) Substance 1 group: STZ(+)+Substance 1 (n=10, 2 cages), and
(4) Comparative Substance 1 group:
  STZ(+)+Comparative Substance 1 (n=10, 2 cages).
After STZ in a dose of 20 mg/kg was intraperitoneally administered for consecutive 4 days (this 4-day administration was performed 2 rounds), STZ in a dose of 40 mg/kg was administered intraperitoneally for consecutive 4 days. Substance 1 or Comparative Substance 1 was mixed into powder feed in 0.06% and the animals were allowed to freely take the feed (from the amount of feed taken a day, the amount of Substance 1 or Comparative Substance 1 taken in per a day was about 100 mg/kg). The administration period was set 5 days before the start of STZ administration and up until 65 days from the start of STZ administration.

Figure 10:
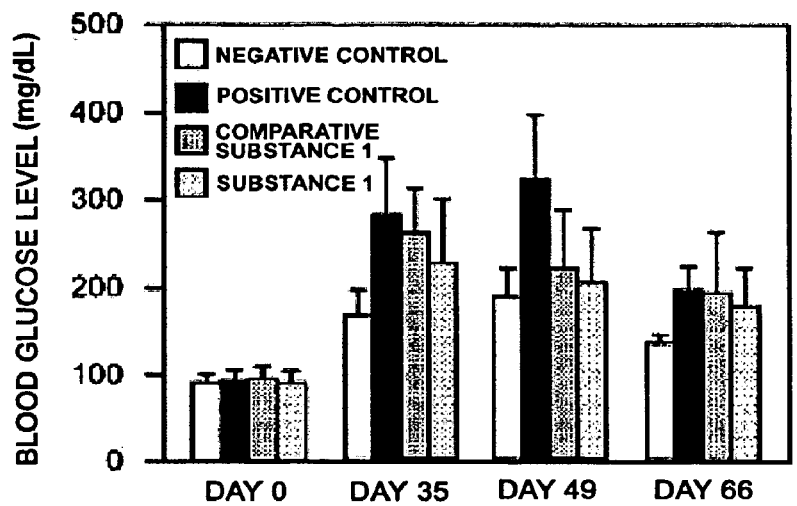
FIG. 10 is a graph illustrating effects of lowering fasting blood glucose level in STZ-induced diabetic mice, with respect to Inventive Substance 1 and Comparative Substance 1.
Figure 11:
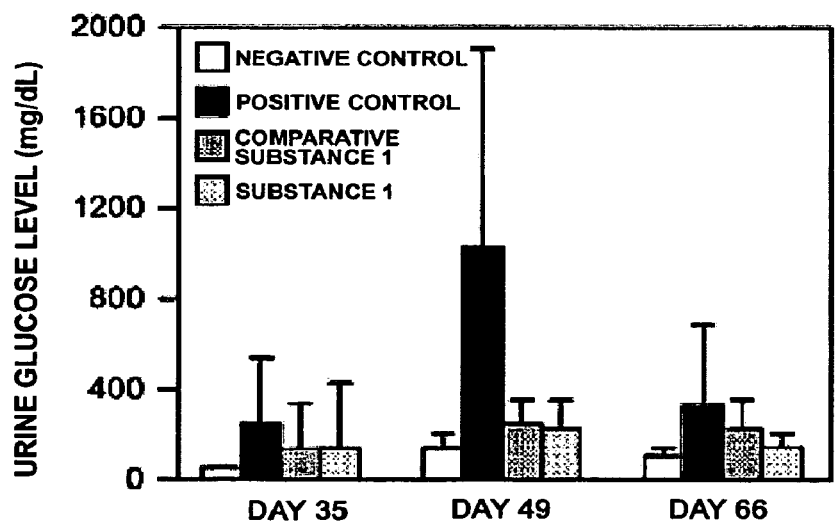
FIG. 11 is a graph illustrating effects of lowering urine glucose level in STZ-induced diabetic mice, with respect to Inventive Substance 1 and Comparative Substance 1.
Figure 12:
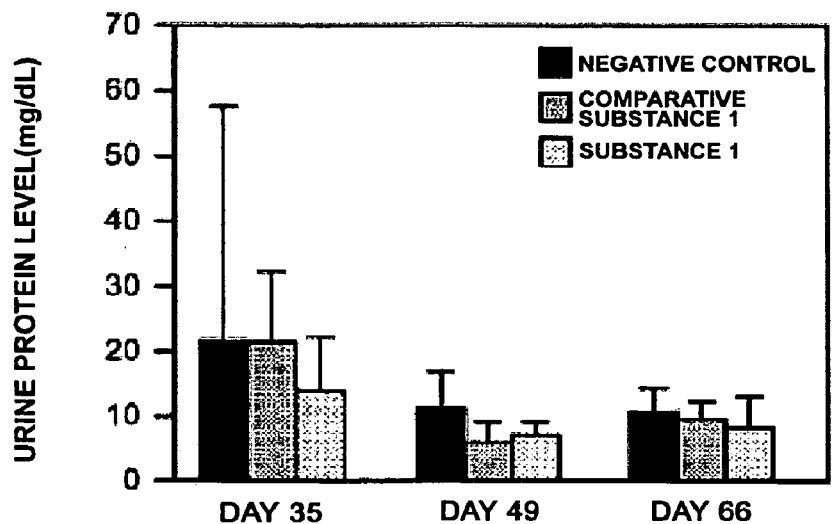
FIG. 12 is a graph illustrating effects of lowering urine protein level in STZ-induced diabetic mice, with respect to Inventive Substance 1 and Comparative Substance 1.
Figure 13:
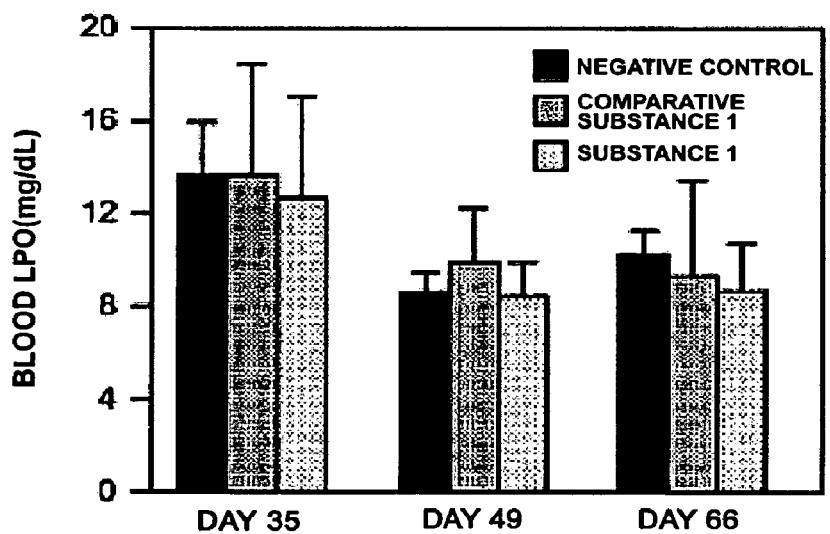
FIG. 13 is a graph illustrating effects of lowering blood PLO level in STZ-induced diabetic mice, with respect to Inventive Substance 1 and Comparative Substance 1.
Figure 14:
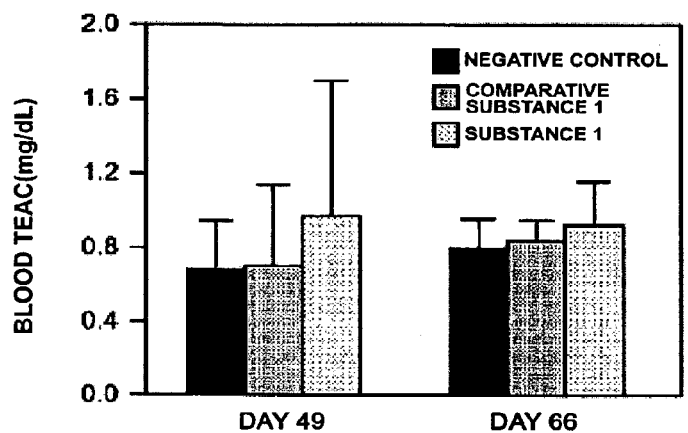
FIG. 14 is a graph illustrating effects of elevating blood TEAC level (antioxidant capacity) in STZ-induced diabetic mice, with respect to Inventive Substance 1 and Comparative Substance 1.

During the administration period, blood and urine were collected and measured for blood glucose, urine glucose, urine protein, blood urea nitrogen (BUN), and blood LPO/TEAC (Trolox equivalent antioxidant capacity). FIGS. 10 to 14 show the measurement results.
[Summary of Results]
(1) Fasting Plasma Glucose Levels In diabetes, the blood glucose level is high when fasting as shown in FIG. 10. On day 35, 49, and 66 after the administration of STZ, the positive control group showed blood glucose levels significantly higher than those of the negative control group and it was confirmed that a mild diabetes model was prepared by administering STZ in multiple low doses. Substance 1 group and Comparative Substance 1 group showed significantly lower blood glucose levels than that of the positive control group and Substance 1 group tended to show a higher effect of lowering the blood glucose level than Comparative Substance 1 group.
(2) Urine Glucose Level In diabetes, the amount of glucose excreted in urine is increased. The amount of glucose excreted in urine is increased greatly by treating STZ, which affirms that diabetes is induced in mice. As shown in FIG. 11, the effect of improving a urine glucose level that increases due to STZ was observed in Substance 1 group and Comparative Substance 1 group, and a significant difference was observed between Substance 1 group and the positive control group and also between Comparative Substance 1 group and the positive control group on Day 49, respectively. Further, Substance 1 group showed relatively low values as compared to those of Comparative Substance 1.
(3) Urine Protein Level In diabetes, the amount of protein excreted in urine is increased. As shown in FIG. 12, Substance 1 and Comparative Substance 1 were able to suppress leakage of protein into urine due to STZ and both the substances significantly reduced the amount of protein on Day 49 from the administration of STZ as compared with the positive control group. Further, it is anticipated that Substance 1 exhibits the effect in earlier stages of this clinical model than Comparative Substance 1.
(4) Antioxidative Capacity Indicator
(4-1) LPO Level in the Blood As shown in FIG. 13, a tendency was observed that Substance 1 group showed lower values than those of the positive control group and Comparative Substance 1 group.
(4-2) Blood TEAC Value TEAC (Trolox equivalent antioxidant capacity) method makes relative evaluation of antioxidation intensity by converting the antioxidation activity of a compound into antioxidant capacity of Trolox, which is an $\alpha$-Tocopherol) derivative. Values obtained by TEAC method are widely used as indicators of antioxidation activity. As shown in FIG. 14, the antioxidation activity values of Comparative Substance 1 group and positive control group were substantially on the same level on Day 49 and Day 66, while the values of Substance group were high to show that the group had the highest antioxidation activity.
[Summary]

In multiple-low-dose STZ models, mild diabetes can be induced in mice and the models do not show much difference among individual models in the blood glucose level as compared with a case using single-high-dose models. Therefore, the multiple-low-dose STZ model may be considered as highly convenient in studying effects of preventing diabetes. Substance 1 was proved to suppress increase in blood glucose level and urine glucose level involved in progress of the clinical condition in the diabetes model and thus have preventive effects against diabetes.

In STZ-induced diabetes, $\beta$ cells injured to death by radicals generated specifically in pancreatic $\beta$ cell induces diabetes. Presumably, by giving Substance 1 and Comparative Substance 1 from 5 days before the administration of STZ, the antioxidation activity in the body can be enhanced in advance, so that injury to $\beta$ cells caused by STZ can be alleviated.

Results of blood LPO and TEAC tests proved that Substance 1 significantly increases blood antioxidant capacity. It is a well-known fact in the art that radicals such as nitrogen monoxide and active oxygen are involved in destruction of pancreatic Langerhans islets in insulin-dependent diabetes, and it is being proved by human-body tests that suppressing cell injury caused by free radicals can alleviate diabetes. Therefore, the results showed that Substance 1 has a preventive effect in healthy persons who are potential candidates for diabetes and further effects of suppressing the progress of clinical conditions in earlier stages of diabetes.

Test Example 7

Comparative Tests on a Rat Model of Potassium Bromate-Induced Acute Kidney Failure In order to elucidate how high the antioxidant capacity of Substance 1 is as compared with other antioxidant polyphenol materials, comparative tests were performed on rat models of potassium bromate-induced acute kidney failure.
[Method]
Wistar rats (male, 12 weeks in age) were divided as follows.
Negative control group: potassium bromate (−) (n=5),
Positive control group: potassium bromate (+) (n=5),
Substance 1 group (derived from grape seeds):
  potassium bromate (+)+Substance 1 (n=5), Substance 5 group (derived from pine bark):
  potassium bromate (+)+Substance 5 (n=5),
Comparative Substance 2 group (catechin):
  potassium bromate (+)+Comparative Substance 2 (n=5),
Comparative Substance 3 group (Ginkgo leaf extract):
  potassium bromate (+)+Comparative Substance 3 (n=5),
Comparative Substance 4 group (derived from pine bark):
  potassium bromate (+)+Comparative Substance 4 (n=5),
Comparative Substance 5 group (cocoa extract):
  potassium bromate (+)+Comparative Substance 5 (n=5), Potassium bromate was intraperitoneally administered in a single dose of 65 mg/kg body weight. Substance 1, Substance 5, and each comparative substance were orally administered every day once a day in a dose of 10 mg/kg body weight before 1 week (Day −7) from start (Day 0) of the administration of potassium bromate up until the day after Day 0. At the day of administration of potassium bromate, the substances were administered 30 minutes before or after the administration of potassium bromate. On Day −7, 0, and 2, blood was collected from the cervical vein and the polyphenol level, lipid peroxide level, TEAC, urea nitrogen level, and creatinine level in the blood were measured.

[Results]

Since the effects of Substance 1 and each comparative substance on potassium bromate-induced acute kidney failure are attributable to antioxidating action, blood polyphenol level, blood antioxidant capacity (TEAC), and blood lipid peroxide level as indicator of antioxidation, and blood urea nitrogen level and blood creatinine level as indicators of clinical outcome in kidney failure were examined. FIGS. 15 to 19 show measurements of these.

(1) Antioxidation Index
(1-1) Blood Polyphenol Level

Figure 15:
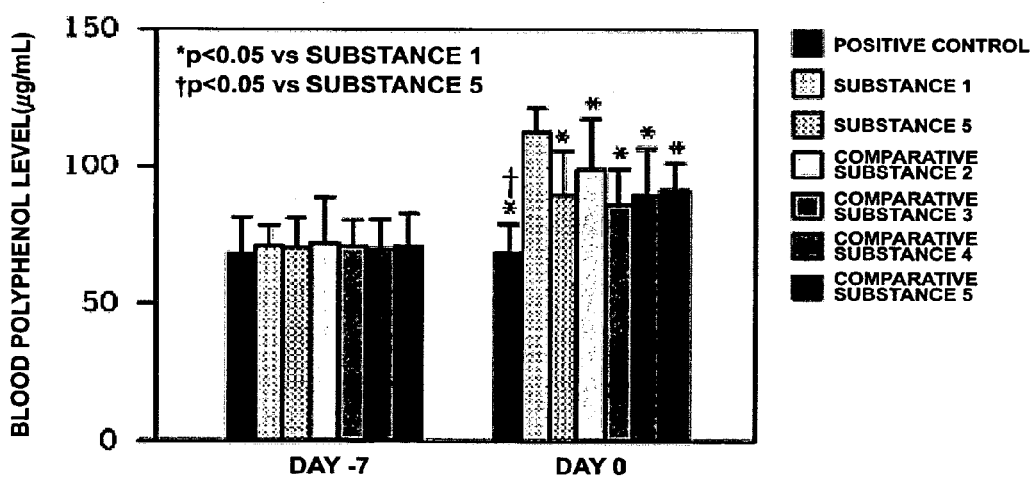
FIG. 15 is a graph illustrating effects of elevating the polyphenol level in the blood in rat models with potassium bromate-induced rat acute renal dysfunction, with respect to Inventive Substance 1.

As shown in FIG. 15, the initial value of blood polyphenol level before the administration of potassium bromate was constant for each group whereas after administration of Substance 1 and each comparative substance for 7 days, Substance 1 group showed the highest value, followed by Comparative Substance 2 group, on Day 0 from the administration of potassium bromate. It was confirmed that the administration of Substance 1 increased blood polyphenol level and its increase rate was significantly higher than that of each comparative substance.

(1-2) Antioxidant Capacity of the Blood (TEAC)

Figure 16:
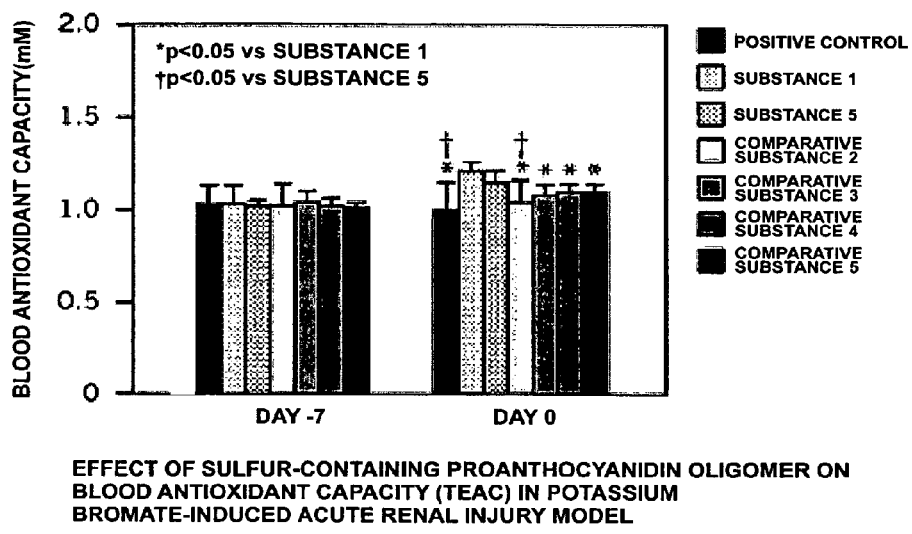
FIG. 16 is a graph illustrating effects of elevating the blood antioxidation activity (TEAC) in rat models with potassium bromate-induced acute renal dysfunction, with respect to Inventive Substance 1.

As shown in FIG. 16, preadministration of Substance 1 and each comparative substance for 1 week caused the blood antioxidant capacity to show a tendency of increase and the increase in antioxidant capacity by the administration of Substance 1 was significant as compared with the groups each administered a comparative substance.

(1-3) Blood Lipid Peroxide Level

Figure 17:
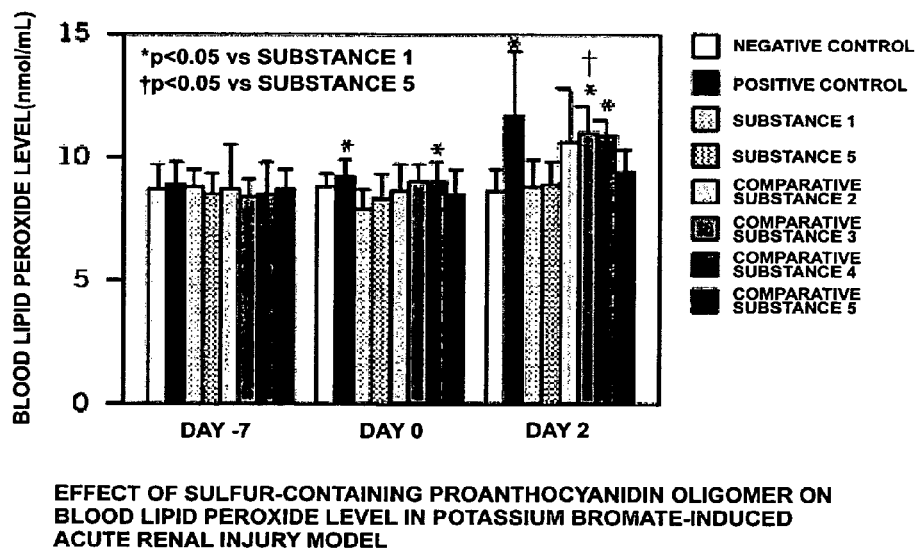
FIG. 17 is a graph illustrating effects of inhibiting elevation of blood lipid peroxide level in rat models with potassium bromate-induced acute renal dysfunction, with respect to Inventive Substance 1.

Preadministration of Substance 1 and each comparative substance for 1 week suppressed increase in blood lipid peroxide level caused by administration of potassium bromate. As shown in FIG. 17, its effect was the highest in Substance 1 group, and Substance 1 group showed a significantly lower value than that of each comparative substance.

(2) Clinical Condition Indices
(2-1) Blood Urea Nitrogen Level

Figure 18:
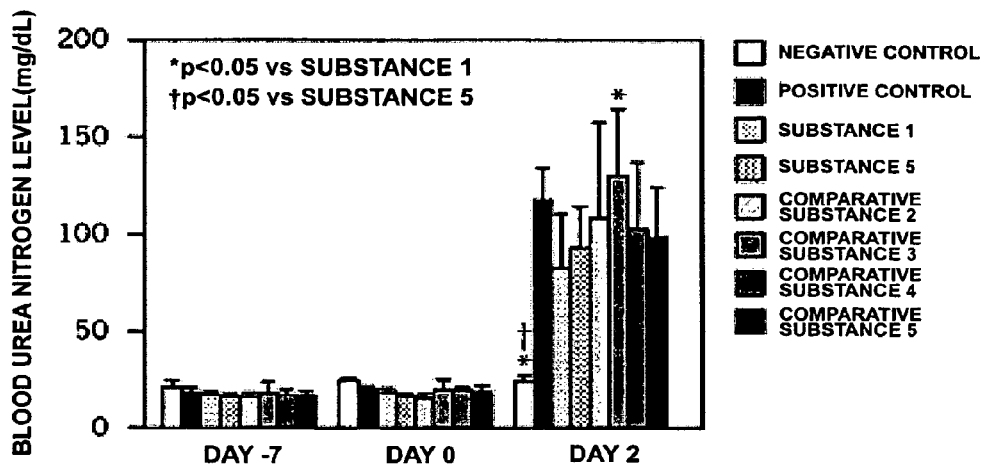
FIG. 18 is a graph illustrating effects of inhibiting elevation of blood urea nitrogen levels in rat models with potassium bromate-induced acute renal dysfunction, with respect to Inventive Substance 1.

As shown in FIG. 18, the administration of potassium bromate significantly increased the blood urea nitrogen level as compared with cases where no treatment was given. Administration of Substance 1 and each comparative substance suppressed the increase in blood urea nitrogen level caused by administration of potassium bromate, and suppression of the increase in blood urea nitrogen level by the administration of Substance 1 was significant as compared with each comparative substance-administered group.

(2-2) Blood Creatinine Level

Figure 19:
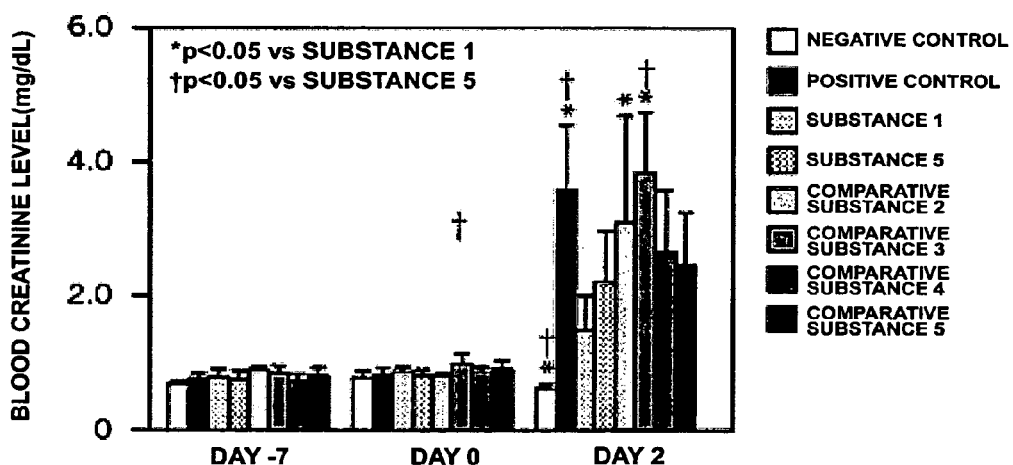
FIG. 19 is a graph illustrating effects of inhibiting elevation of blood creatinine levels in rat models with potassium bromate-induced acute renal dysfunction, with respect to Inventive Substance 1.

As shown in FIG. 19, administration of potassium bromate significantly increased the blood creatinine level as compared with cases where no treatment was given. Administration of Substance 1 and each comparative substance suppressed the increase in blood creatinine level caused by the administration of potassium bromate, and the suppression of the increase in blood creatinine level by the administration of Substance 1 was significant as compared with each comparative substance-administered group.

[Summary]

Comparative Substances 3, 4, and 5 are materials rich in proanthocyanidin polymer (high molecular weight) and show high antioxidation activity in vitro. However, Substance 1 with a reduced molecular weight was higher than each comparative substance in the antioxidation activity when taken in by an organism. As compared to Comparative Substance 2 which is a monomer (catechin), Substance 1 showed a still higher activity. From the amount of polyphenol in blood, it was proved that Substance with a reduced molecular has excellent absorbability into a living body and exhibits antioxidation activity in the organism. Preadministration of Substance 1 increased blood antioxidant capacity and exhibited antioxidation activity. As a result, this suppressed increase in blood lipid peroxide level caused by the administration of potassium bromate, suppressed kidney failure, and thereby suppressed leakage of urea nitrogen and creatinine into blood. The effect thereof was significantly higher than that of each comparative substance, and excellent in antioxidation property when taken in by an organism as compared with a polyphenol material based on high molecular weight polyphenol and monomer (catechin) thus far known.

[Safety of Inventive Substance]

Safety was evaluated by single dose administration toxicity tests. That is, Substance 1 was forcibly orally administered in does of 2.5, 5.0, 7.5, and 10.0 g per kg body weight to 8, 7, 3, and 18 ddY mice (9 weeks in age, male), respectively. Changes in behavior and death after the administration were observed and LC50 was calculated. As a result, 50% lethal concentration (LC50) of Substance 1 was 5.0 g/kg body weight (95% reliability limit: 3.5 to 6.4 g/kg body weight). Further, no abnormality in the behavior after the administration or no abnormality in observation of dissection when the tests were completed were observed. The above results confirmed that Substance 1 is extremely safe as food.

In the above-mentioned Test Example 4 (monitoring test on human beings), comments of test subjects were collected by questionnaire. Of those, Table 10 shows results relating to sleeping, and Table 11 shows the results of fatigue, clearheadedness, and stomach function by 5-phase evaluation.

TABLE 10

| Group | Age | Sex | Comments after use |
|---|---|---|---|
| Substance 1 | 49 | Male | Became a good riser. |
| Substance 1 | 43 | Male | Quality of sleep was improved. |
| Substance 1 | 57 | Male | Pleasant awakening in the morning. |
| Comparative Substance 1 | 27 | Female | Feeling of fatigue when getting up. |
| Comparative Substance 1 | 34 | Male | Sleepy and hard to get up. |

TABLE 10-continued

| Group | Age | Sex | Comments after use |
|---|---|---|---|
| Comparative Substance 1 | 43 | Male | Became a bad riser. |

TABLE 11

| | Average score of questionnaire by 5-phase evaluation | | |
|---|---|---|---|
| | Feeling of fatigue | Clear-headedness | Stomach function |
| Comparative Substance 1 | 2.8 (3.2) | 3.7 (3.3) | 3.9 (3.5) |
| Substance 1 | 3.2 (2.9) | 3.7 (3.3) | 3.8 (3.5) |

(Greater numbers indicate better conditions; numbers in the brackets are those before administration)

The invention claimed is:

1. An isolated compound represented by Formula (5).

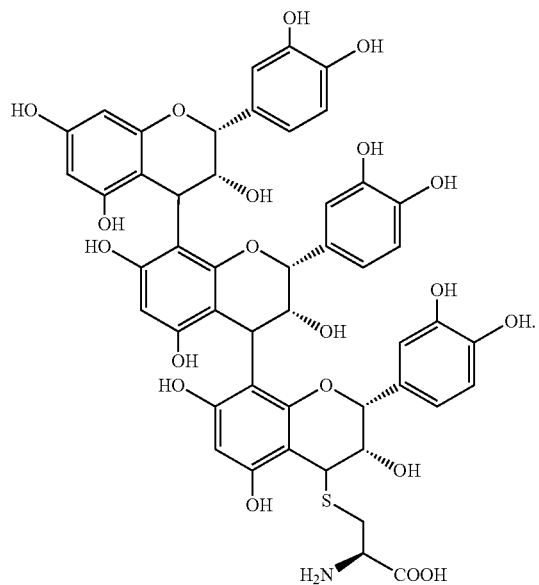

(5)

* * * * *